(12) United States Patent
Bowman et al.

(10) Patent No.: US 6,323,351 B1
(45) Date of Patent: Nov. 27, 2001

(54) PROCESS FOR THE DIRECT OXIDATION OF OLEFINS TO OLEFIN OXIDES

(75) Inventors: Robert G. Bowman; Alex Kuperman; Howard W. Clark; George E. Hartwell, all of Midland, MI (US); Garmt R. Meima, Terneuzen (NL)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/458,136

(22) Filed: Dec. 9, 1999

Related U.S. Application Data

(63) Continuation of application No. PCT/US97/24270, filed on Dec. 18, 1997.

(51) Int. Cl.[7] .................. C07D 308/06; C07D 308/10
(52) U.S. Cl. ................ 549/536; 549/537; 549/538
(58) Field of Search ................... 549/536, 537, 549/538

(56) References Cited

U.S. PATENT DOCUMENTS

| | | |
|---|---|---|
| 3,957,690 | 5/1976 | Bobolev et al. . |
| 3,959,316 | 5/1976 | Piccinini et al. . |
| 4,007,135 | 2/1977 | Hayden et al. . |
| 4,242,235 | 12/1980 | Cognion et al. . |
| 4,400,308 | 8/1983 | Alter et al. . |
| 4,410,501 | 10/1983 | Taramasso et al. . |
| 4,689,316 | 8/1987 | Bowman . |
| 4,845,253 | 7/1989 | Bowman . |
| 4,950,773 | * 8/1990 | Monnier et al. . |
| 5,145,968 | 9/1992 | Monnier et al. . |
| 5,380,697 | 1/1995 | Matusz et al. . |
| 5,525,741 | 6/1996 | Sugita et al. . |
| 5,703,254 | 12/1997 | Gaffney et al. . |
| 5,859,265 | 1/1999 | Müller et al. . |
| 5,965,754 | 10/1999 | Clark et al. . |

FOREIGN PATENT DOCUMENTS

| | | |
|---|---|---|
| 0 640 598 A1 | 3/1995 | (EP) . |
| 0 709 360 B1 | 12/1998 | (EP) . |
| 012 489 | 5/1978 | (JP) . |
| 4-352771 | 12/1992 | (JP) . |
| 96/02323 | 2/1996 | (WO) . |
| 97/25143 | 7/1997 | (WO) . |
| 97/34693 | 9/1997 | (WO) . |
| 97/47386 | 12/1997 | (WO) . |
| WO 97/43617 | 12/1997 | (WO) . |
| 99/52883 | 10/1999 | (WO) . |
| WO 00/07964 | 2/2000 | (WO) . |

OTHER PUBLICATIONS

"Activation and Regeneration of a Hydro–Oxidation Catalyst", filed in the United States on Dec. 9, 1999, USSN 60/169,862 (Attorney's Docket No. 44361); Applicant: Deborah H. Parker et al.

"Method of Preparing a Catalyst Containing Gold and Titanium", filed in the United States on Apr. 8, 1999, USSN 60/128,390 (Attorney's Docket No. 44251); Applicant: Alex Kuperman et al.

"Process for the Hydro–Oxidation of Olefins to Olefin Oxides", filed in the United States on Apr. 8, 1999, USSN 60/128,394 (Attorney's Docket No. 44406): Applicant: Alex Kuperman et al.

"Process for Direct Oxidation of Olefins to Olefin Oxides", filed in the United States on Dec. 16, 1998, USSN 60/112,429 (Attorney's Docket No. 44172); Applicant: Robert G. Bowman et al.

"Process for Direct Oxidation of Olefins to Olefin Oxides"; filed in the United States on Dec. 11, 1988, USSN 09/209,700 (Attorney's Docket No. 42637D); Applicant: Robert G. Bowman et al.

"Process for Direct Oxidation of Olefins to Olefin Oxides", filed in the United States on Dec. 9, 1999, USSN 09/458,559 (Attorney's Docket No. 42637D–DIV1); Applicant: Robert G. Bowman et al.

"Process for Direct Oxidation of Olefins to Olefin Oxides", filed in the United States on December 11, 1998, USSN 09/209,698 (Attorney's Docket No. 42637F); Applicant: Robert G. Bowman et al.

Chemical Abstract, 98:71265x (1983).

* cited by examiner

Primary Examiner—T. A. Solola
(74) Attorney, Agent, or Firm—Marie F. Zuckerman

(57) ABSTRACT

A process and catalysts for the direct oxidation of an olefin having three or more carbon atoms, such as propylene, by oxygen to an olefin oxide, such as propylene oxide. The process involves contacting the olefin under reaction conditions with oxygen in the presence of hydrogen and a catalyst. The catalyst contains silver and titanium, optionally gold, and optionally, at least one promoter element selected from Group 1, Group 2, zinc, cadmium, the lanthanide rare earths, and the actinide elements. Suitable supports include titanium dioxide, titanium dioxide on silica, titanosilicates, promoter metal titanates, titanium dispersed on silica and promoter metal silicates.

45 Claims, No Drawings

PROCESS FOR THE DIRECT OXIDATION OF OLEFINS TO OLEFIN OXIDES

CROSS REFERENCE TO RELATED APPLICATIONS

This application is a continuation of International Patent Application No. PCT/US97/24270, filed Dec. 18, 1997, which claims the benefit of International Patent Application PCT/US 97/11414, filed Jun. 30, 1997; the benefit of International Patent Application PCT/US 97/11417, filed Jun. 30, 1997; and the benefit of International Patent Application PCT/US 97/11415, filed Jun. 30, 1997.

This invention was made with United States Government support under Award Number 70NANB5H1143 awarded by the National Institute of Standards and Technology. The United States Government has certain rights in the invention.

BACKGROUND OF THE INVENTION

This invention pertains to a process and catalyst for the direct oxidation of olefins, such as propylene, by oxygen to olefin oxides, such as propylene oxide.

Olefin oxides, such as propylene oxide, are used to alkoxylate alcohols to form polyether polyols, such as polypropylene polyether polyols, which find significant utility in the manufacture of polyurethanes and synthetic elastomers. Olefin oxides are also important intermediates in the manufacture of alkylene glycols, such as propylene glycol and dipropylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide. This process suffers from the production of a low concentration salt stream. (See K. Weissermel and H. J. Arpe, *Industrial Organic Chemistry*, $2^{nd}$ ed., VCH Publishers, Inc., New York, N.Y., 1993, p. 264–265.)

Another well-known route to olefin oxides relies on the transfer of an oxygen atom from an organic hydroperoxide or peroxycarboxylic acid to an olefin. In the first step of this oxidation route, a peroxide generator, such as isobutane or acetaldehyde, is autoxidized with oxygen to form a peroxy compound, such as t-butyl hydroperoxide or peracetic acid. This compound is used to epoxidize the olefin, typically in the presence of a transition metal catalyst, including titanium, vanadium, molybdenum, and other heavy metal compounds or complexes. Along with the olefin oxide produced, this process disadvantageously produces equimolar amounts of a coproduct, for example an alcohol, such as t-butanol, or an acid, such as acetic acid, whose value must be captured in the market place. (*Industrial Organic Chemistry*, ibid., p. 265–269.)

Metal-catalyzed processes for the direct oxidation of propylene by oxygen are known. For example, U.S. Pat. No. 5,525,741 discloses the direct oxidation of propylene with oxygen in the presence of a crystalline metallosilicate, such as titanosilicate, having supported thereon a silver salt of nitric or nitrous acid. This patent is silent with respect to conducting the process in the presence of hydrogen.

PCT publication WO-A1-96/02323 discloses the hydrooxidation of an olefin, including propylene, with oxygen in the presence of hydrogen and a catalyst to form an olefin oxide. The catalyst is a titanium or vanadium silicalite containing at least one platinum group metal, and optionally, an additional metal selected from silver, iron, cobalt, nickel, rhenium, and gold.

The aforementioned direct oxidations employ catalysts which are deficient in activity and/or selectivity to propylene oxide.

PCT publication WO-A1-97/25143 discloses the hydrooxidation of an olefin, including propylene, with oxygen in the presence of hydrogen and a catalyst to form the corresponding olefin oxide. The catalyst is a titanium or vanadium silicalite containing a lanthanide metal. Optionally, an additional metal selected from the Group 8 metals of the Periodic Table, rhenium, silver, and gold may be incorporated into the catalyst. Catalysts consisting of a lanthanide metal and a titanium or vanadium silicate exhibit low activity to propylene oxide.

In view of the above, a need continues to exist in the chemical industry for an efficient direct route to propylene oxide and higher olefin oxides from the reaction of oxygen with $C_3$ and higher olefins. The discovery of such a process which simultaneously achieves high selectivity to the olefin oxide at an economically advantageous conversion of the olefin would represent a significant achievement over the prior art.

This invention is a novel process of preparing an olefin oxide directly from an olefin and oxygen and hydrogen. The process comprises contacting an olefin having at least three carbon atoms with oxygen in the presence of hydrogen and a catalyst under process conditions sufficient to produce the corresponding olefin oxide. The catalyst which is employed in the process of this invention comprises silver and titanium. In another aspect of the process of this invention, the catalyst comprising silver and titanium can further comprise gold, or at least one promoter element as noted hereinafter, or a combination of gold with one or more promoter elements.

The novel process of this invention is useful for producing an olefin oxide directly from oxygen and hydrogen and an olefin having three or more carbon atoms. Under preferred process conditions, the olefin oxide is produced in a high selectivity at a good conversion of the olefin.

In another aspect, this invention is a unique catalyst composition comprising silver, at least one promoter element, and a titanium-containing support. The promoter element is selected from Group 1, Group 2, zinc, cadmium, the rare earth lanthanides, and the actinide elements, as well as combinations of these elements.

In a third aspect, this invention is a unique catalyst composition comprising silver, gold, and a titanium-containing support. Optionally, this catalyst can contain at least one promoter element selected from Group 1, Group 2, zinc, cadmium, the rare earth lanthanides, and the actinide elements, including combinations thereof.

The novel compositions of this invention can be effectively used in the aforementioned direct oxidation of an olefin having three or more carbon atoms to the corresponding epoxide. In preferred embodiments, the catalysts achieve a high selectivity to olefin oxide at a good conversion of the olefin. When the catalyst is partially or completely spent, it is easy to regenerate. Accordingly, this composition possesses desirable properties for catalyzing the direct oxidation of propylene and higher olefins to their corresponding olefin oxides.

DETAILED DESCRIPTION OF THE INVENTION

The novel process of this invention comprises contacting an olefin having three or more carbon atoms with oxygen in the presence of hydrogen and an epoxidation catalyst under process conditions sufficient to prepare the corresponding olefin oxide. In one preferred embodiment, a diluent is employed, as described in detail hereinafter. The relative molar quantities of olefin, oxygen, hydrogen, and optional diluent can be any which are sufficient to prepare the desired olefin oxide. In a preferred embodiment of this invention, the olefin employed is a $C_{3-12}$ olefin, and it is converted to the corresponding $C_{3-12}$ olefin oxide. In a more preferred embodiment, the olefin is a $C_{3-8}$ olefin, and it is converted to the corresponding $C_{3-8}$ olefin oxide. In a most preferred embodiment, the olefin is propylene, and the olefin oxide is propylene oxide.

The catalyst employed in the aforementioned process of this invention comprises silver and titanium. In a preferred embodiment, the catalyst comprising silver and titanium is essentially free of the Group 8 metals. The Group 8 metals include iron, cobalt, nickel, ruthenium, rhodium, palladium, osmium, iridium, and platinum. The term "essentially free," as used in this context, means that the total concentration of these metals is less than about 0.01 weight percent, preferably, less than about 0.005 weight percent, based on the total weight of the catalyst composition.

In another preferred embodiment, the catalyst comprises silver, gold, and a titanium-containing support. This catalyst embodiment is also essentially free of the Group 8 metals, as defined hereinbefore.

In yet another preferred embodiment, the catalyst comprises silver and at least one promoter element on a titanium-containing support. The promoter is selected from Group 1, Group 2, zinc, cadmium, the rare earth lanthanides, and the actinides of the Periodic Table of the Elements, as referenced in the *CRC Handbook of Chemistry and Physics,* 75th edition, CRC Press, 1994–1995. Combinations of the aforementioned promoters can also be employed. In a more preferred embodiment, the support excludes a Group 2 metal titanate. In still another preferred embodiment, the catalyst comprises silver, gold, and at least one promoter selected from Group 1, Group 2, zinc, cadmium, the rare earth lanthanides, and the actinide elements, on a titanium-containing support.

Any olefin containing three or more carbon atoms can be employed in the process of this invention. Monoolefins are preferred, but compounds containing two or more carbon—carbon double bonds, such as dienes, can also be used. The olefin can be a simple hydrocarbon containing only carbon and hydrogen atoms; or alternatively, the olefin can be substituted at any of the carbon atoms with an inert substituent. The term "inert", as used herein, requires the substituent to be substantially non-reactive in the process of this invention. Suitable inert substituents include, but are not limited to, halides, ether, ester, alcohol, and aromatic moieties, preferably chloro, $C_{1-12}$ ether, ester, and alcohol moieties and $C_{6-12}$ aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, α-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin employed in the process can vary over a wide range provided that the corresponding olefin oxide is produced. Generally, the quantity of olefin depends upon the specific process features, including for example, the design of the reactor, the specific olefin, and economic and safety considerations. Those skilled in the art will know how to determine a suitable range of olefin concentrations for the specific process features. Typically, on a molar basis an excess of olefin is used relative to the oxygen, because this condition enhances the productivity to olefin oxide. In light of the disclosure herein, the quantity of olefin is typically greater than about 1, preferably, greater than about 10, and more preferably, greater than about 20 mole percent, based on the total moles of olefin, oxygen, hydrogen, and optional diluent. Typically, the quantity of olefin is less than about 99, preferably, less than about 85, and more preferably, less than about 70 mole percent, based on the total moles of olefin, oxygen, hydrogen, and optional diluent.

Oxygen is also required for the process of this invention. Any source of oxygen is acceptable, including air and essentially pure molecular oxygen. Other sources of oxygen may be suitable, including ozone and nitrogen oxides, such as nitrous oxide. Molecular oxygen is preferred. The quantity of oxygen employed can vary over a wide range provided that the quantity is sufficient for producing the desired olefin oxide. Ordinarily, the number of moles of oxygen per mole of olefin is less than 1. Under these conditions the selectivity to olefin oxide is enhanced while the selectivity to combustion products, such as carbon dioxide, is minimized. Preferably, the quantity of oxygen is greater than about 0.01, more preferably, greater than about 1, and most preferably greater than about 5 mole percent, based on the total moles of olefin, hydrogen, oxygen, and optional diluent. Preferably, the quantity of oxygen is less than about 30, more preferably, less than about 25, and most preferably less than about 20 mole percent, based on the total moles of olefin, hydrogen, oxygen, and optional diluent. Above about 20 mole percent, the concentration of oxygen may fall within the flammable range for olefin-hydrogen-oxygen mixtures.

Hydrogen is also required for the process of this invention. In the absence of hydrogen, the activity of the catalyst is significantly decreased. Any source of hydrogen can be used in the process of this invention including for example, molecular hydrogen obtained from the dehydrogenation of alkanes and alcohols. In an alternative embodiment, the hydrogen may be generated in situ in the olefin oxidation process, for example, by dehydrogenating alkanes, such as propane or isobutane, or alcohols, such as isobutanol. Alternatively, hydrogen can be used to generate a catalyst-hydride complex or a catalyst-hydrogen complex which can supply the necessary hydrogen to the process.

Any quantity of hydrogen can be employed in the process provided that the amount is sufficient to produce the olefin oxide. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably less than about 20 mole percent, based on the total moles of olefin, hydrogen, oxygen, and optional diluent.

In addition to the above reagents, it may be desirable to employ a diluent in the reaction mixture, although the use thereof is optional. Since the process of this invention is exothermic, a diluent beneficially provides a means of removing and dissipating the heat produced. In addition, the diluent provides an expanded concentration regime in which the reactants are non-flammable. The diluent can be any gas or liquid which does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. Most of these gases are essentially inert with respect to the process of this invention. Carbon dioxide and steam may not necessarily be inert, but may have a beneficial promoting effect. If the process is conducted in a liquid phase, then the diluent can be any oxidation stable and thermally stable liquid. Suitable liquid diluents include aromatics, such as benzene; chlorinated aromatics, such as chlorobenzene and dichlorobenzene; aliphatic alcohols, such as methanol; chlorinated aliphatic alcohols, such as chloropropanol; as well as liquid polyethers, polyesters, and polyalcohols.

If used, the amount of diluent is typically greater than about 0.01, preferably greater than about 0.1, and more preferably, greater than about 15 mole percent, based on the total moles of olefin, oxygen, hydrogen, and optional diluent. The amount of diluent is typically less than about 90, preferably, less than about 80, and more preferably, less than about 70 mole percent, based on the total moles of olefin, oxygen, hydrogen, and diluent.

The concentrations of olefin, oxygen, hydrogen, and diluent disclosed hereinabove are suitably based on the reactor designs and process parameters disclosed herein. Those skilled in the art will recognize that concentrations other than those disclosed herein may be suitably employed in other various engineering realizations of the process.

Unique catalysts which are beneficially employed in the process of this invention comprise silver and titanium. The silver can exist as individual atoms and/or in discrete silver particles and/or, if a promoter is used, in mixed silver-promoter particles. The formal oxidation state of the silver can be any oxidation state or combination of states that provides for an active catalyst.

In another aspect, unique catalysts which are beneficially employed in the process of this invention comprise silver and gold and titanium. The silver can exist as individual atoms and/or in discrete silver particles and/or in silver-gold particles and/or, if a promoter is used, in mixed silver-gold-promoter particles. The formal oxidation state of the silver and/or the gold can be any oxidation state or combination of states that provides for an active catalyst.

The titanium preferably is present as a titanium-containing support which may take a variety of forms. The titanium predominantly exists in a positive oxidation state, as determined by X-ray photoelectron and X-ray absorption spectroscopies. More preferably, the titanium exists in an oxidation state of about +2 or higher, most preferably, in an oxidation state of about +3 to about +4. Non-limiting examples of titanium-containing supports which can be suitably employed in the catalyst of this invention include those described hereinbelow. Titanium-containing supports noted hereinbelow which do not contain the desired promoter element(s) must be treated to incorporate the promoter (s) into or onto the support. Supports already containing promoters may or may not require extra promoter element(s) to be added to the support.

a. Titanium Dioxide

Amorphous and crystalline titanium dioxide can be suitably employed as the titanium-containing support. The crystalline phases include anatase, rutile, and brookite. Included in this category are composites comprising titanium dioxide supported on silica, alumina, aluinosilicates, or other supports or combinations of supports.

The titanium dioxide may be deposited on the support in a number of methods. One example of the preparation which may be used herein is given by M. Haruta et al. in the European Patent Application EP 0709360A1, incorporated herein by reference. More generally, the support may be calcined in air to a temperature between 50° C. and 800° C. prior to the deposition of the titanium compound. The support is then impregnated with a titanium compound which is poorly reactive with the surface hydroxyls on the support. Typically, a solution containing the titanium compound is contacted with the support under mild conditions, such as a temperature between about 0° C. and about 50° C., at about ambient pressure for a time ranging from about 30 minutes to about 24 hours. A non-limiting example of a suitable titanium compound includes titanium oxide acetylacetonate or titanyl acetylacetonate. The solvent can be any which solubilizes the titanium compound, for example, aliphatic alcohols or aliphatic and aromatic hydrocarbons. After contacting the support with the solution containing the titanium compound, the support is dried at a temperature between about 0° C. and about 150° C., preferably between about 50° C. and about 150° C., in a vacuum or in a stream of air or an inert gas, such as nitrogen, argon, or helium. Thereafter, the support can be calcined in air to a temperature between about 300° C. and about 800° C., preferably between about 400° C. and about 650° C.

b. Promoter Metal Titanates

Stoichiometric and non-stoichiometric compounds comprising promoter metal titanates can also be suitably employed as the catalyst support. The promoter metal titanates can be crystalline or amorphous. Non-limiting examples of these include the titanates of Group 1, Group 2, and the lanthanide and actinide metals. Preferably, the promoter metal titanate is selected from the group consisting of magnesium titanate, calcium titanate, barium titanates, strontium titanate, sodium titanate, potassium titanate, and the titanates of erbium, lutetium, thorium, and uranium.

c. Titanosilicates

Crystalline and amorphous titanosilicates, preferably those that are porous, are also suitably employed as the support. Titanosilicates can be microporous materials incorporating Ti in the structure; these may be zeolitic materials. Within the framework structure of porous titanosilicates there exists a regular or irregular system of pores and/or channels. Empty cavities, referred to as cages, can also be present. The pores can be isolated or interconnecting, and they can be one, two, or three dimensional. The pores are more preferably micropores or mesopores or some combination thereof. As used herein, a micropore has a pore diameter (or critical dimension as in the case of a non-circular perpendicular cross-section) ranging from about 4 Å to about 20 Å, while a mesopore has a pore diameter or critical dimension ranging from greater than about 20 Å to about 500 Å. The combined volume of the micropores and the mesopores preferably comprises about 70 percent or greater of the total pore volume, and more preferably, about 80 percent or greater of the total pore volume. The balance of the pore volume will comprise macropores, which have a pore diameter of greater than about 500 Å. Macropores include the void spaces between particles or crystallites.

The pore diameter (or critical dimension), pore size distribution, and surface area of the porous titanosilicate can be obtained from the measurement of adsorption isotherms and pore volume. Typically, the measurements are made on the titanosilicate in powder form using as an adsorbate nitrogen at 77 K or argon at 88 K and using any suitable adsorption analyzer, such as a Micromeritics ASAP 2000 instrument. Measurement of micropore volume is derived from the adsorption volume of pores having a diameter in the range from about 4 Å to about 20 Å. Likewise, measurement of mesopore volume is derived from the adsorption volume of pores having a diameter in the range from greater than about 20 Å to about 500 Å. From the shape of the adsorption isotherm, a qualitative identification of the type of porosity, for example, microporous or macroporous, can be made. Additionally, increased porosity can be correlated with increased surface area. Pore diameter (or critical dimension) can be calculated from the data using equations described by Charles N. Satterfield in *Heterogeneous Catalysis in Practice,* McGraw-Hill Book Company, New York, 1980, pp. 106–114, incorporated herein by reference.

Additionally, crystalline porous titanosilicates can be identified by X-ray diffraction methods (XRD), either by comparing the XRD pattern of the material of interest with a previously published standard or by analyzing the XRD pattern of a single crystal to determine framework structure, and if pores are present, the pore geometry and pore size.

Non-limiting examples of porous titanosilicates which are suitably employed in the process of this invention include porous amorphous titanosilicates; porous layered titanosilicates; crystalline microporous titanosilicates, such as titanium silicalite-1 (TS-1), titanium silicalite-2 (TS-2), titanosilicate beta (Ti-beta), titanosilicate ZSM-12 (Ti-ZSM-12) and titanosilicate ZSM-48 (Ti-ZSM-48); as well as mesoporous titanosilicates, such as Ti-MCM-41.

Titanium silicalite and its characteristic XRD pattern have been reported in U.S. Pat. No. 4,410,501, incorporated herein by reference. TS-1 can be obtained commercially, but it can also be synthesized following the methods described in U.S. Pat. No. 4,410,501. Other preparations have been reported by the following (incorporated herein by reference): A. Tuel, *Zeolites,* 1996, 16, 108–117; by S. Gontier and A. Tuel, *Zeolites,* 1996, 16, 184–195; by A. Tuel and Y. Ben Taarit in *Zeolites,* 1993, 13, 357–364; by A. Tuel, Y. Ben Taarit and C. Naccache in *Zeolites,* 1993, 13, 454–461; by A. Tuel and Y. Ben Taarit in *Zeolites,* 1994, 14, 272–281; and by A. Tuel and Y. Ben Taarit in *Microporous Materials,* 1993, 1, 179–189.

TS-2 can be synthesized by the methods described in the following references (incorporated herein by reference): J. Sudhakar Reddy and R. Kumar, *Zeolites,* 1992, 12, 95–100; by J. Sudhakar Reddy and R. Kumar, *Journal of Catalysis,* 1991, 130, 440–446; and by A. Tuel and Y. Ben Taarit, Applied Catal. A, General, 1993, 102, 69–77.

The structure and preparation of titanosilicate beta have been described in the following references, incorporated herein by reference: PCT patent publication WO 94/02245 (1994); M. A. Camblor, A. Corma, and J. H. Perez-Pariente, Zeolites, 1993, 13, 82–87; and M. S. Rigutto, R. de Ruiter, J. P. M. Niederer, and H. van Bekkum, *Stud. Surf. Sci. Cat.,* 1994, 84, 2245–2251.

The preparation and structure of Ti-ZSM-12 are described by S. Gontier and A. Tuel, ibid., incorporated herein by reference.

References to the preparation and structure of Ti-ZSM-48 include R. Szostak, *Handbook of Molecular Sieves,* Chapman & Hall, New York, 1992, p. 551–553; as well as C. B. Dartt, C. B. Khouw, H. X. Li, and M. E. Davis, *Microporous Materials,* 1994, 2, 425–437; and A. Tuel and Y. Ben Taarit, *Zeolites,* 1996, 15, 164–170. The aforementioned references are incorporated herein by reference.

Ti-MCM-41, its structure, and preparation are described in the following citations incorporated herein by reference: S. Gontier and A. Tuel, *Zeolites,* 1996, 15, 601–610; and M. D. Alba, Z. Luan, and J. Klinowski, J. Phys. Chem., 1996, 100, 2178–2182.

The silicon to titanium atomic ratio (Si/Ti) of the titanosilicate can be any ratio which provides for an active and selective epoxidation catalyst in the process of this invention. A generally advantageous Si/Ti atomic ratio is equal to or greater than about 5/1, preferably, equal to or greater than about 10/1. A generally advantageous Si/Ti atomic ratio is equal to or less than about 200/1, preferably, equal to or less than about 100/1. It is noted that the Si/Ti atomic ratio defined herein refers to a bulk ratio which includes the total of the framework titanium and the extra-framework titanium. At high Si/Ti ratios, for example, about 100/1 or more, there may be little extra-framework titanium and the bulk ratio essentially corresponds to the framework ratio.

d. Titanium Dispersed on a Support

Another suitable support for the catalyst of this invention comprises titanium dispersed on a support such as silica, alumina, aluminosilicates, or any other support or combinations of supports. This support can be obtained commercially, or alternatively, prepared by the methods described hereinbelow.

In the aforementioned support, the titanium ions are dispersed over the surface of the silica substantially in a disorganized phase. The titanium ions in the disorganized phase may be isolated from other titanium ions, or alternatively, the titanium ions may be linked through oxide bonds to other titanium ions in small domains of a two-dimensional monolayer network. Whatever its actual topology, the disorganized phase does not exhibit an organized, periodic crystallinity. The disorganized phase can be distinguished from a bulk organized phase by one or more modern analytical techniques, for example, high resolution transmission electron microscopy and Raman spectroscopy. Ultraviolet visible diffuse reflectance spectroscopy and titanium K edge X-ray absorption near edge structure spectroscopy may also be useful. These techniques and others are known to those skilled in the art.

Any silica can be used in the support provided that it allows for an active catalyst composition. The silicas can be amorphous or crystalline. Preferred silicas are surface hydroxylated. Non-limiting examples of suitable silicas include fumed silica, silica gel, precipitated silicas, precipitated silica gels, silicalite, and mixtures thereof. Preferably, the surface area of the silica is greater than about 15 $m^2/g$, more preferably, greater than about 20 $m^2/g$, and most preferably, greater than about 25 $m^2/g$. More preferably, the surface area of the silica is less than about 800 $m^2/g$, most preferably, less than about 600 $m^2/g$.

Any alumina can be used in the support provided that it allows for an active catalyst composition. The aluminas can be amorphous or crystalline. Preferred aluminas are surface hydroxylated. Preferably, the surface area of the alumina is greater than about 15 $m^2/g$, more preferably, greater than about 20 $m^2/g$, and most preferably, greater than about 25 $m^2/g$. More preferably, the surface area of the alumina is less than about 800 $m^2/g$, most preferably, less than about 600 $m^2/g$.

The titanium loading on the support can be any which gives rise to an active catalyst in the process of this invention. Typically, the titanium loading is greater than about 0.02 weight percent, preferably, greater than about 0.1 weight percent, based on the weight of the support. Typically, the titanium loading is less than about 20 weight percent, and preferably less than about 10 weight percent, based on the weight of the support.

The method of depositing the titanium ions on the support is important in obtaining the disorganized titanium phase described hereinabove. A description along the lines of the preparation used herein is given by S. Srinivasan et al. in the *Journal of Catalysis,* 131, 260–275 (1991), and by R. Castillo et al., *Journal of Catalysis,* 161, 524–529 (1996), incorporated herein by reference. Generally, the support is impregnated with a titanium compound which is reactive with the surface hydroxyls on the support. Typically, a solution containing a reactive titanium compound is contacted with the silica under mild conditions, such as a temperature between about 0° C. and about 50° C., at about ambient pressure for a time ranging from about 30 minutes to about 24 hours. Non-limiting examples of suitably reactive titanium compounds include titanium alkoxides, such as titanium isopropoxide, titanium propoxide, titanium ethoxide, and titanium butoxide; titanium sulfate, titanium oxysulfate, titanium halides, preferably titanium chloride; titanium carboxylates, preferably titanium oxalate; and organotitanium halides, such as dicyclopentadiene titanium dichloride, and other organotitanocene dichlorides. Preferably, titanium alkoxides are employed. The solvent can be any which solubilizes the reactive titanium compound, for example, aliphatic alcohols, aliphatic and aromatic hydrocarbons, and water where appropriate. After contacting the support with the solution containing the reactive titanium compound, the support is dried at a temperature between about 0° C. and about 150° C., preferably between about 50° C. and about 150° C., in a vacuum or in a stream of air or an inert gas, such as nitrogen, argon, or helium. Thereafter, the support can be used without calcination or further treatment. Alternatively after drying, the support can be calcined in air or an inert gas, such as nitrogen or helium, to a temperature between about 100° C. and about 800° C., preferably between about 100° C. and about 650° C.

An alternate method of deposition of the titanium is from the vapor phase. Volatile titanium compounds, such as titanium chloride, titanium propoxide, or titanium isopropoxide, can be carried through the support in a flow of an inert gas such as nitrogen, argon, or helium. The titanium compound can be heated to volatilize or vaporize it into the inert gas stream. The support can be heated during the process. Thereafter, the support can be used without calcination or further treatment. Alternatively, the support can be calcined in air or an inert gas, such as nitrogen or helium, to a temperature between about 100° C. and about 800° C., preferably between about 100° C. and about 650° C.

e. Titanium Dispersed on Promoter Metal Silicates

Yet another suitable support for the catalyst of this invention comprises titanium dispersed on promoter metal silicates. Stoichiometric and non-stoichiometric compounds comprising promoter metal silicates can be used. Any amorphous or crystalline promoter metal silicate is suitably employed. Preferred promoter metal silicates include the silicates of Group 1, Group 2, the lanthanide rare earths, and the actinide metals, and combinations thereof. Non-limiting examples of preferred promoter metal silicates include sodium containing silicate, cesium containing silicate, magnesium silicate, calcium silicate, barium silicate, erbium silicate, and lutetium silicate. The titanium can be dispersed on the promoter metal silicate in a manner analogous to that described in section (d) hereinabove. Analytical methods such as those described in section (d) hereinabove can be used to identify the dispersed titanium phase.

f. Mixtures of Supports

Any combination or mixture of the supports a–e, described hereinabove, can be employed in the catalyst of this invention.

The silver loading on the titanium-containing supports (a–f) can be any which gives rise to the catalyst of this invention. The silver can be added either before, simultaneously with, or after the titanium is added to the support. Generally, the silver loading is greater than about 0.01, preferably, greater than about 0.02 weight percent, based on the total weight of the catalyst composition. Generally, the silver loading is less than about 20, preferably, less than about 15 weight percent.

The silver component can be deposited or supported on the support by any method known in the art which provides for an active and selective epoxidation catalyst in the process of this invention. Non-limiting examples of known deposition methods include impregnation, ion-exchange, and deposition by precipitation. A preferred method involves contacting the support with a solution of a soluble silver compound. Aqueous and non-aqueous solutions can be employed. The preparation can be done in the presence of light or in the dark. Then, the composite is calcined and optionally reduced to form the catalyst of the invention.

For aqueous solutions, any water soluble silver compound can be used including silver nitrate and silver carboxylates, such as silver oxalate and silver lactate. For non-aqueous solutions of common organic solvents, any soluble silver complex, such as a silver amine complex, can be used. Typically, the molarity of the soluble silver compound ranges from about 0.001 M to the saturation point of the soluble silver compound, preferably, from about 0.005 M to about 0.5 M. The desired quantity of support is added to the solution, and the mixture is stirred under air at a temperature between about 20° C. and about 80° C. for a time ranging from about 1 hour to about 24 hours. At the end of this period, the solids are either recovered or dried. The solids are not washed, or optionally lightly washed with water, the water optionally containing one or more promoter salts. Thereafter, the composite is dried at a temperature between about 80° C. and about 120° C., and then calcined, in the presence of oxygen at a temperature between about 200° C. and about 800° C., preferably from about 350° C. to about 750° C., for a time from about 1 to about 24 hours. The calcination may be used to decompose the anion of the silver salt, such as the nitrate or lactate. Optionally, the calcined material may be reduced with a liquid or gas phase reducing agent, such as hydrogen, ammonia, or hydrazine, at a temperature between about 20° C. and about 500° C., preferably between about 100° C. and about 400° C., for a time from about 1 to about 24 hours to form the catalyst of this invention.

As noted hereinbefore, in one preferred embodiment the catalyst comprising silver and the titanium-containing support is essentially free of Group 8 metals, including iron, cobalt, nickel, ruthenium, rhodium, palladium, osmium, iridium, and platinum. The term "essentially free," as used in these context, means that the total concentration of these metals is less than about 0.01 weight percent, preferably, less than about 0.005 weight percent, based on the weight of the total catalyst composition.

In another preferred embodiment, the catalyst comprising silver on the titanium-containing support further comprises gold. Preferably, this catalyst also is essentially free of the Group 8 metals, as noted hereinbefore. Generally, the gold loading is greater than about 0 weight percent, preferably, greater than about 0.01 weight percent, based on the total weight of the catalyst composition. Generally, the gold loading is less than about 20 weight percent, preferably, less than about 10 weight percent. The gold present may be in any oxidation state. The gold may be present as an alloy with the silver.

The gold can be deposited onto the titanium-containing support simultaneously with the silver, or alternatively, in a separate deposition step either before or after silver is deposited. The gold component can be deposited or supported on the support by any method known in the art which provides for an active and selective epoxidation catalyst in the process of this invention. Non-limiting examples of known deposition methods include impregnation, ion-exchange, and deposition by precipitation. A preferred deposition method is disclosed by S. Tsubota, M. Haruta, T. Kobayashi, A. Ueda, and Y. Nakahara, "Preparation of Highly Dispersed Gold on Titanium and Magnesium Oxide," in *Preparation of Catalysts* V, G. Poncelet, P. A. Jacobs, P. Grange, and B. Delmon, eds., Elsevier Science Publishers B.V., Amsterdam, 1991, p. 695ff, incorporated herein by reference. This method involves contacting the support with an aqueous solution of a soluble gold compound at a temperature and pH sufficient to deposit or react the gold compound onto the support. Non-aqueous solutions can also be employed. Thereafter, the silver component can be deposited on the support in the manner described hereinbefore. Thereafter, the composite containing silver and gold is not washed or is lightly washed, with preferably no more than about 100 ml wash liquid per gram composite. Then, the silver-gold composite is calcined under air at a temperature between about 150° C. and about 800° C. for a time from about 1 to 24 hours. The calcined material may then be heated in a reducing atmosphere, such as hydrogen, or heated in an inert atmosphere, such as nitrogen, at a temperature between about 150° C. and about 800° C. for a time from about 1 to 24 hours.

For aqueous solutions, any water soluble gold compound can be used, such as chloroauric acid, sodium chloroaurate, potassium chloroaurate, gold cyanide, potassium gold cyanide, and diethylamine auric acid trichloride. Typically, the molarity of the soluble gold compound ranges from about 0.001 M to the saturation point of the soluble gold compound, preferably, from about 0.005 M to about 0.5 M. The pH of the aqueous gold solution may be adjusted to between about 2 and about 11, preferably, between about 6 and about 9, with any suitable base, such as Group 1 metal hydroxides or carbonates, preferably sodium hydroxide, sodium carbonate, potassium carbonate, cesium hydroxide, and cesium carbonate. The desired quantity of support is added to the solution, or vice versa; and if necessary, the pH is again adjusted. Thereafter, the mixture is stirred under air at a temperature between about 20° C. and about 80° C. for a time ranging from about 1 hour to about 24 hours. At the end of this period, the solids are recovered, optionally washed with water, the water optionally containing one or more promoter metal salts preferably at a pH between about 5 and about 11. Thereafter, the solids are dried under air at a temperature between about 80° C. and about 120° C. Afterwards, the solids are treated with a solution containing a silver compound in the manner described hereinbefore. The silver-gold-support composite is calcined under air at a temperature between about 150° C. and about 800° C. for a time from about 1 to 24 hours. The calcined material may then be heated in a reducing atmosphere, such as hydrogen, or heated in an inert atmosphere, such as nitrogen, at a temperature between about 150° C. and about 800° C. for a time from about 1 to 24 hours.

In another preferred embodiment, the catalyst comprising silver and titanium or the catalyst comprising silver, gold, and a titanium-containing support contains one or more promoter elements. Any metal ion having a valence between +1 and +7 which enhances the productivity of the catalyst in the oxidation process can be employed as a promoter element. Factors contributing to increased productivity of the catalyst include increased conversion of the olefin, increased selectivity to the olefin oxide, decreased production of water, and increased catalyst lifetime. Preferred promoter elements include the elements of Groups 1 and 2 of the Periodic Table of the Elements, as well as zinc, cadmium, the rare earth lanthanides and actinides, as referenced in the *CRC Handbook of Chemistry and Physics*, $75^{th}$ ed., CRC Press, 1994. Group 1 elements include lithium, sodium, potassium, rubidium, and cesium; Group 2 elements include beryllium, magnesium, calcium, strontium, and barium. The lanthanide rare earth elements include cerium, praseodymium, neodymium, promethium, samarium, europium, gadolinium, terbium, dysprosium, holmium, erbium, thulium, ytterbium, and lutetium. The actinide elements specifically include for the purposes of this invention thorium and uranium. More preferably, the promoter element is sodium, cesium, magnesium, calcium, barium, lanthanum, praseodymium, erbium, or lutetium. Even more preferably, the catalyst contains one or more promoter elements with the proviso that when a lanthanide element is used, it is in combination with a Group 1 and/or a Group 2 element. Most preferably, the catalyst contains a combination of at least one Group 1 element with a Group 2 element and/or a lanthanide element.

If one or more promoter elements are used, then the total quantity of promoter element(s) deposited on the support typically is greater than about 0.001 weight percent, and preferably, greater than about 0.01 weight percent, based on the total weight of the catalyst composition. The total quantity of promoter element(s) deposited on the support is generally less than about 40, preferably, less than about 20 weight percent, based on the total weight of the catalyst. Those skilled in the art will recognize that when a promoter metal titanate or silicate is employed, the weight percentage of promoter metal may be much higher, for example, as high as about 80 weight percent The promoter element(s) can be deposited onto the titanium-containing support simultaneously with the silver, or alternatively, in a separate deposition step either before or after silver is deposited. When gold is in the preparation, the promoter element(s) can be deposited onto the titanium-containing support simultaneously with the silver and/or gold, or alternatively, in a separate deposition step either before or after silver and/or gold are deposited. Alternatively, the promoter element can be deposited onto a precursor form of the catalyst before the titanium is added, or after it is added, or simultaneously with the titanium. Typically, the promoter element is deposited from an aqueous or organic solution containing a soluble promoter metal salt. Any salt of the promoter metal with adequate solubility can be used; for example, the metal nitrates, carboxylates, and halides, preferably, the nitrates, are suitable. If an organic solvent is employed, it can be any of a variety of known organic solvents, including, for example, alcohols, esters, ketones, and aliphatic and aromatic hydrocarbons. Ordinarily, the support is contacted with the solution of the promoter metal salt under conditions which are similar to those used for contacting the support with the silver solution. After the promoter metal is deposited, washing is optional, and if done to excess, can leach at least a portion of the promoter element out of the catalyst. Afterwards, calcination under air and optionally reduction with a reducing agent are conducted in a manner similar to that described hereinabove for the silver deposition.

Optionally, the catalyst of this invention can be extruded with, bound to, or supported on a second support, such as silica, alumina, an aluminosilicate, magnesia, titania, carbon, or mixtures thereof. The second support may function to improve the physical properties of the catalyst, such as, its strength or attrition resistance, or to bind the catalyst particles together. Generally, the quantity of second support ranges from about 0 to about 95 weight percent, based on the combined weight of the catalyst and second support.

The process of this invention can be conducted in a reactor of any conventional design suitable for gas or liquid phase processes. These designs broadly include batch, fixed-bed, transport bed, fluidized bed, moving bed, shell and tube, and trickle bed reactors, as well as continuous and intermittent flow and swing reactor designs. Preferably, the process is conducted in the gas phase and the reactor is designed with heat transfer features for the removal of the heat produced. Preferred reactors designed for these purposes include fluidized bed and moving bed reactors, as well as swing reactors constructed from a plurality of catalyst beds connected in parallel and used in an alternating fashion.

The process conditions for the direct oxidation described herein can vary considerably over a nonflammable and flammable regime. It is beneficial, however, to recognize the conditions which distinguish between nonflammable and flammable mixtures of the olefin, hydrogen, and oxygen. Accordingly, a diagram can be constructed or consulted which for any given process temperature and pressure shows the flammable and non-flammable range of reactant compositions, including the diluent, if used. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the process is conducted at a temperature which is greater than about ambient, taken as 20° C., preferably, greater than about 70° C. Usually, the process is conducted at a temperature less than about 250° C., preferably less than about 225° C. Preferably, the pressure ranges from about atmospheric to about 400 psig (2758 kPa).

In flow reactors the residence time of the reactants and the molar ratio of reactants to catalyst will be determined by the space velocity. For a gas phase process the gas hourly space velocity (GHSV) of the olefin can vary over a wide range, but typically is greater than about 10 ml olefin per ml catalyst per hour ($h^{-1}$) preferably greater than about 100 $h^{-1}$, and more preferably, greater than about 1,000 $h^{-1}$. Typically, the GHSV of the olefin is less than about 50,000 $h^{-1}$, preferably, less than about 35,000 $h^{-1}$, and more preferably, less than about 20,000 $h^{-1}$. Likewise, for a liquid phase process the weight hourly space velocity (WHSV) of the olefin component may vary over a wide range, but typically is greater than about 0.01 g olefin per g catalyst per hour ($h^{-1}$), preferably, greater than about 0.05 $h^{-1}$, and more preferably, greater than about 0.1 $h^{-1}$. Typically, the WHSV of the olefin is less than about 100 $h^{-1}$, preferably, less than about 50 $h^{-1}$, and more preferably, less than about 20 $h^{-1}$. The gas and weight hourly space velocities of the oxygen, hydrogen, and diluent components can be determined from the space velocity of the olefin taking into account the relative molar ratios desired.

When an olefin having at least three carbon atoms is contacted with oxygen in the presence of hydrogen and the catalyst described hereinabove, the corresponding olefin oxide (epoxide) is produced in good productivity. The most preferred olefin oxide produced is propylene oxide.

The conversion of olefin in the process of this invention can vary depending upon the specific process conditions employed, including the specific olefin, temperature, pressure, mole ratios, and form of the catalyst. As used herein the term "conversion" is defined as the mole percentage of olefin which reacts to form products. Generally, the conversion increases with increasing temperature and pressure and decreases with increasing space velocity. Typically, the olefin conversion is greater than about 0.02 mole percent, and preferably, greater than about 0.10 mole percent, and more preferably, greater than about 0.20 percent.

Likewise, the selectivity to olefin oxide can vary depending upon the specific process conditions employed. As used herein, the term "selectivity" is defined as the mole percentage of reacted olefin which forms a particular product, desirably the olefin oxide. Generally, the selectivity to olefin oxide will decrease with increasing temperature and will increase with increasing space velocity. The process of this invention produces olefin oxides in unexpectedly high selectivity. A typical selectivity to olefin oxide in this process is greater than about 60 mole percent, preferably, greater than about 75 mole percent, and more preferably, greater than about 90 mole percent.

Besides the epoxide formed, water is also formed as a by-product of the process of this invention. Additionally, hydrogen may be reacted directly to form water. Accordingly, it may be desirable to achieve a water/olefin oxide molar ratio as low as possible. In preferred embodiments of this invention, the water/olefin oxide molar ratio is typically greater than about 1/1, but less than about 75/1, and preferably, less than about 50/1, and more preferably, less than about 20/1.

When the activity of the catalyst has decreased to an unacceptably low level, the catalyst can be regenerated. Any catalyst regeneration method known to those skilled in the art can be applied to the catalyst of this invention, provided that the catalyst is reactivated for the oxidation process described herein. One regeneration method comprises heating the deactivated catalyst at a temperature between about 150° C. and about 500° C. in a regeneration gas containing oxygen and optionally an inert gas. In an alternative embodiment, water is beneficially added to the regeneration gas in an amount preferably ranging from about 0.01 to about 100 mole percent.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a mole percent basis.

EXAMPLES

Example 1

Silver nitrate (1.1720 g) was dissolved in water (30 cc). Titanium dioxide (Alfa/Aesar anatase, 15.01 g) was added to the silver solution, and the mixture was stirred for 1.5 hours at room temperature. Then, the mixture was dried overnight at 110° C. The dried material was crushed, then calcined under a mixture of oxygen (20 percent) in helium as follows. The temperature was raised from room temperature to 500° C. in 8 hours and maintained at 500° C. under the oxygen/helium mixture for 5 hours. Afterwards, the sample was cooled to room temperature. The calcined material was heated from room temperature to 300° C. over 4 hours in a mixture of hydrogen (5 percent) in helium and held at 300° C. for 4 hours under the hydrogen mixture. The sample was cooled to room temperature to yield a catalyst comprising silver on titanium dioxide.

The catalyst prepared hereinabove was tested in the hydro-oxidation of propylene to propylene oxide. The catalyst (5 g) was loaded into a 10 cc fixed-bed, continuous flow reactor with flows of helium, oxygen, hydrogen, and propylene. Total flow rate was 150 cc/min (or GHSV 1,800 h$^{-1}$). Feedstream composition was 11 percent hydrogen, 10 percent oxygen, 30 percent propylene, and the balance helium. Propylene, oxygen and helium were used as pure streams; hydrogen was mixed with helium in a 20 H$_2$/80 He (v/v) mixture. Pressure was atmospheric; reactor temperature was 70° C. Products were analyzed using an on-line gas chromatograph (Chrompack™ Poraplot™ S column, 25 m) with the results shown in Table I.

TABLE I

Direct Oxidation of Propylene (PP) to Propylene Oxide (PO) Over Ag/TiO$_2$ Catalyst[a]

| Ex. | Time on Stream | Conv PP (mol %) | Sel PO (mol %) | H$_2$O/PO |
|---|---|---|---|---|
| 1 | | 0.210 | 10.1 | 377 |
| 2 | | 0.043 | 42.9 | 197 |
| Regenerated at 350° C. under oxygen | | | | |
| 1 | 5 min | 0.056 | 46.9 | 309 |
| 1 | 45 min | 0.035 | 52.2 | 316 |
| 2 | 5 min | 0.037 | 71.4 | 158 |
| 2 | 45 min | 0.026 | 70.0 | 147 |

[a]Feedstream (mol %): 11% H$_2$, 10% O$_2$, 30% propylene, balance helium; flow 150 cc/min; 70° C.; pressure atmospheric; 5 wt percent Ag on TiO$_2$.

The catalyst was regenerated by heating at 350° C. in a flow of oxygen (15 percent) in helium for 2 hours. The regenerated catalyst was retested in the oxidation of propylene with the results shown in Table I.

It is seen that a composition comprising silver on titanium dioxide is capable of catalyzing the hydro-oxidation of propylene to propylene oxide. Catalyst selectivity to propylene oxide improved after regeneration.

Example 2

A catalyst was prepared in the manner described in Example 1. The following amounts of reagents were used: titanium dioxide (Degussa P25 anatase, 15.00 g), silver nitrate (1.1358 g), and water (60 cc). The catalyst was tested in the hydro-oxidation of propylene to propylene oxide with the results shown in Table I. The catalyst was regenerated by heating at 350° C. in a flow of oxygen (15 percent) in helium for 2 hours. The regenerated catalyst was retested in the oxidation of propylene with the results shown in Table I.

It is seen that a composition comprising silver on titanium dioxide is capable of catalyzing the hydro-oxidation of propylene to propylene oxide. Catalyst selectivity and hydrogen efficiency, as measured by the water/propylene oxide molar ratio, are improved when a Degussa titanium dioxide is used as opposed to the Alfa/Aesar titanium dioxide. Catalyst is also improved after regeneration.

Example 3 (a–c)

Three catalysts comprising silver on titanium dioxide were prepared in the manner described in Example 1. The quantities of titanium dioxide (Degussa P25 titanium dioxide) used were as follows: (a) 14.94 g; (b) 15.06 g); (c) 15.00 g. The quantities of silver nitrate used were as follows: (a) 1.1238 g; (b) 2.2706 g; (c) 3.4053 g. Water (60 cc) was used in each preparation. Elemental analysis, as analyzed by neutron activation analysis (NAA), for 3(a) was the following: 3.95 weight percent silver; 0.29 weight percent sodium; and 55.4 weight percent titanium. (The titanium dioxide used was found to contain 0.27 percent sodium.) The silver concentration for examples 3(b) and 3(c) were approximately 10 and 15 weight percent. The catalysts were tested in the hydro-oxidation of propylene to propylene oxide in the manner described in Example 2 with the results shown in Table II.

TABLE II

Propylene (PP) to Propylene Oxide (PO) Over Ag/TiO$_2$ Catalyst[a]

| Catalyst | Approx. Wt % Ag | Hours On Stream | Conv (mol %). | Sel (mol %). | H$_2$O/PO |
|---|---|---|---|---|---|
| 50° C. | | | | | |
| 3a | 4 | 0.3 | 0.030 | 93.1 | 60 |
| 3b | 10 | 0.5 | 0.028 | 80.8 | 91 |
| 3c | 15 | 0.7 | 0.026 | 57.7 | 150 |
| 60° C. | | | | | |
| 3a | 4 | 1.1 | 0.033 | 75.0 | 142 |
| 3b | 10 | 1.3 | 0.020 | 60.0 | 197 |
| 3c | 15 | 1.5 | 0.023 | 42.9 | 397 |
| 70° C. | | | | | |
| 3a | 4 | 1.9 | 0.025 | 36.0 | 502 |
| 3b | 10 | 2.1 | 0.025 | 60.0 | 288 |
| 3c | 15 | 2.3 | 0.030 | 33.3 | 571 |

[a]Feedstream (mol %): 11% hydrogen, 10% oxygen, 30% propylene, balance helium; flow 150 cc/min; pressure atmospheric.

Example 4

Four catalysts (4a–d) were prepared to test the effect of silver loading with the use of a magnesium-promoted silver on titania catalyst. Degussa P25 titanium dioxide was used to prepare the catalysts. The amounts of reagents are shown in Table III. The amount of magnesium nitrate was kept constant in each sample. Thus, the atomic ratio of magnesium to silver was different for each sample.

TABLE III

Reagents used for Ag and Mg on TiO$_2$

| Sample | TiO$_2$ | AgNO$_3$ | Mg(NO$_3$)$_2$.6H$_2$O | Mg/Ag |
|---|---|---|---|---|
| 4a | 15.04 g | 0.5719 g | 0.5001 g | 0.58 |
| 4b | 15.03 g | 1.1267 g | 0.5041 g | 0.30 |
| 4c | 15.02 g | 2.2617 g | 0.5052 g | 0.15 |
| 4d | 14.99 g | 3.4043 g | 0.4987 g | 0.10 |

The silver nitrate and magnesium nitrate were dissolved in water (60 cc). The titanium dioxide was added to the silver and magnesium solution, and the solution was stirred for 1 hour at room temperature. The flask containing the mixture was placed in a drying oven at 110° C. overnight. The resulting dried material was crushed and then calcined from room temperature to 500° C. in 8 hours and held at 500° C. for 5 hours in a mixture of oxygen (20 percent) in helium. The calcined material was cooled to room temperature, then heated in a mixture of hydrogen (5 percent) in helium from room temperature to 300° C. in 4 hours and held at 300° C. for 4 hours.

The catalysts were tested in the hydro-oxidation of propylene to propylene oxide, in the manner described in Example 2 with the results shown in Table IV.

TABLE IV

Propylene (PP) to Propylene Oxide (PO) Over Ag(Mg)/TiO$_2$ Catalyst[a]

| Catalyst | Approx. Wt % Ag | Hour On Stream | Conv. (mol %) | Sel. (mol %) | H$_2$O/PO |
|---|---|---|---|---|---|
| 50° C. | | | | | |
| 4a | 2.5 | 0.1 | 0.000 | 0.0 | — |
| 4b | 5 | 0.3 | 0.091 | 72.3 | 31 |
| 4c | 10 | 0.5 | 0.056 | 66.7 | 67 |
| 4d | 15 | 0.7 | 0.045 | 65.9 | 87 |
| 60° C. | | | | | |
| 4a | 2.5 | 0.9 | 0.025 | 75.0 | 106 |
| 4b | 5 | 1.1 | 0.080 | 73.0 | 74 |
| 4c | 10 | 1.3 | 0.047 | 54.5 | 171 |
| 4d | 15 | 1.5 | 0.037 | 44.1 | 265 |
| 70° C. | | | | | |
| 4a | 2.5 | 1.7 | 0.043 | 73.2 | 100 |
| 4b | 5 | 1.9 | 0.057 | 50.9 | 234 |
| 4c | 10 | 2.1 | 0.041 | 38.5 | 370 |
| 4d | 15 | 2.3 | 0.042 | 30.8 | 464 |

[a]Feedstream (mol %): 11% hydrogen, 10% oxygen, 30% propylene, balance helium; flow 150 cc/min; pressure atmospheric When the data in Example 4 is compared with the data in Experiments 1–3, it is seen that the magnesium promoter improved catalyst performance in terms of conversion of propylene and selectivity to propylene oxide. In addition, the water/propylene oxide molar ratio was reduced when the promoter element was used.

Example 5

Eight catalysts were prepared to test the effect of different promoters (P) with a catalyst comprising silver on titania (Degussa P25). The reagents and the quantities of each used in the preparation are shown in Table V. The silver was kept constant at about 5 weight percent on titania. The amount of promoter nitrate was kept constant in each sample. This changed the atomic ratio of promoter to silver (P/Ag) in each sample, as shown in Table V. The preparation method was similar to Example 4 with the exception that the calcination profile was as follows: Calcined from room temperature to 500° C. in 4 hours and held at 500° C. for 5 hours in 20 percent oxygen in helium. Then, the materials were cooled to 80° C., heated in 5 percent hydrogen in helium from 80° to 300° C. in 4 hours and held at 300° C. for 4 hours. Elemental analysis, as analyzed by NAA for 5(a) was the following: 4.17 percent silver; 1.03 percent sodium, and 54.4 percent titanium, as weight percentages. The transmission electron microscopy revealed that the silver crystallites ranged in size from 15–90 Å in the fresh catalyst with an average diameter of 44 Å.

TABLE V

Reagents used for Ag and (Promoter) on TiO$_2$

| Ex. | TiO$_2$ | AgNO$_3$ | Promoter Nitrate | P/Ag |
|---|---|---|---|---|
| 5a | 15.01 g | 1.1175 g | NaNO$_3$ 0.4768 g | 0.85 |
| 5b | 15.09 g | 1.1215 g | CsNO$_3$ 0.4717 g | 0.37 |
| 5c | 15.05 g | 1.1254 g | Ca(NO$_3$)$_2$.4H$_2$O 0.5060 g | 0.32 |
| 5d | 15.03 g | 1.1262 g | Ba(NO$_3$)$_2$ 0.4965 g | 0.29 |
| 5e | 15.02 g | 1.1278 g | La(NO$_3$)$_3$.6H$_2$O 0.4869 g | 0.17 |
| 5f | 15.01 g | 1.1250 g | Pr(NO$_3$)$_3$.xH$_2$O 0.4736 g | 0.17 |
| 5g | 15.00 g | 1.1298 g | Er(NO$_3$)$_3$.5H$_2$O 0.4979 g | 0.17 |
| 5h | 15.03 g | 1.1269 g | Lu(NO$_3$)$_3$.xH$_2$O 0.4979 g | 0.17 |

Catalyst samples 5a–5h were tested in the hydro-oxidation of propylene to propylene oxide, in the manner described in Example 1, with the results shown in Table VI.

TABLE VI

Ag(P)/TiO$_2$ Reactivity at Various Temperatures[a]

| Catalyst | Promoter (P) | P/Ag | Hour on Stream | Sel. mol % | Conv. mol % | H$_2$O/PO |
|---|---|---|---|---|---|---|
| 50° C. | | | | | | |
| 5a | Na | 0.85 | 0.1 | 100.0 | 0.013 | 23 |
| 5b | Cs | 0.37 | 0.5 | 93.8 | 0.052 | 37 |
| 5c | Ca | 0.32 | 0.3 | 97.6 | 0.134 | 16 |
| 5d | Ba | 0.29 | 0.5 | 97.9 | 0.102 | 25 |
| 5e | La | 0.17 | 0.3 | 81.8 | 0.105 | 46 |
| 5f | Pr | 0.17 | 0.1 | 67.3 | 0.053 | 41 |
| 5g | Er | 0.17 | 0.7 | 93.3 | 0.098 | 27 |
| 5h | Lu | 0.17 | 0.9 | 93.3 | 0.048 | 41 |
| 60° C. | | | | | | |
| 5a | Na | 0.85 | 1.3 | 100.0 | 0.098 | 20 |
| 5b | Cs | 0.37 | 1.7 | 94.7 | 0.060 | 72 |
| 5c | Ca | 0.32 | 1.5 | 92.1 | 0.136 | 30 |
| 5d | Ba | 0.29 | 1.7 | 92.1 | 0.107 | 41 |
| 5e | La | 0.17 | 1.5 | 77.5 | 0.094 | 97 |
| 5f | Pr | 0.17 | 1.3 | 75.7 | 0.107 | 64 |
| 5g | Er | 0.17 | 1.9 | 85.2 | 0.095 | 53 |
| 5h | Lu | 0.17 | 2.1 | 90.0 | 0.062 | 54 |
| 70° C. | | | | | | |
| 5a | Na | 0.85 | 2.5 | 100.0 | 0.164 | 19 |
| 5b | Cs | 0.37 | 2.9 | 95.2 | 0.066 | 111 |
| 5c | Ca | 0.32 | 2.7 | 86.8 | 0.122 | 51 |
| 5d | Ba | 0.29 | 2.9 | 85.3 | 0.101 | 56 |
| 5e | La | 0.17 | 2.7 | 62.7 | 0.071 | 250 |
| 5f | Pr | 0.17 | 2.5 | 54.2 | 0.075 | 178 |
| 5g | Er | 0.17 | 3.1 | 75.0 | 0.060 | 126 |
| 5h | Lu | 0.17 | 3.3 | 86.5 | 0.055 | 68 |
| 80° C. | | | | | | |
| 5a | Na | 0.85 | 3.7 | 100.0 | 0.217 | 20 |
| 5b | Cs | 0.37 | 4.1 | 60.0 | 0.078 | 209 |
| 5c | Ca | 0.32 | 3.9 | 84.1 | 0.114 | 60 |
| 5d | Ba | 0.29 | 4.1 | 83.3 | 0.095 | 58 |
| 5e | La | 0.17 | 3.9 | 61.0 | 0.062 | 295 |
| 5f | Pr | 0.17 | 3.7 | 69.2 | 0.041 | 160 |
| 5g | Er | 0.17 | 4.3 | 71.7 | 0.049 | 156 |
| 5h | Lu | 0.17 | 4.5 | 86.7 | 0.048 | 75 |

TABLE VI-continued

Ag(P)/TiO$_2$ Reactivity at Various Temperatures[a]

| Catalyst | Promoter (P) | P/Ag | Hour on Stream | Sel. mol % | Conv. mol % | H$_2$O/PO |
|---|---|---|---|---|---|---|
| Regenerated at 350° C. in oxygen: | | | | | | |
| 80° C. | | | | | | |
| 5a | Na | 0.85 | 1.1 | 100.0 | 0.201 | |
| 5b | Cs | 0.37 | 0.5 | 94.3 | 0.090 | |
| 5c | Ca | 0.32 | 0.3 | 51.5 | 0.144 | |
| 5d | Ba | 0.29 | 0.5 | 85.7 | 0.137 | |
| 5g | Er | 0.17 | 0.7 | 77.4 | 0.069 | |
| 5h | Lu | 0.17 | 0.9 | 86.7 | 0.048 | |

(a) Feedstream (mol %): 11% hydrogen, 10% oxygen, 30% propylene, balance helium; Catalyst: 5% Ag (P)/TiO$_2$; flow 150 cc/min; atmospheric pressure.

It is seen that compositions comprising silver, a promoter element selected from Group 1, Group 2, or the lanthanides, and titanium dioxide functioned as catalysts in the hydro-oxidation of propylene to propylene oxide. When Example 5 is compared with Examples 1 and 2, it is seen that the addition of the promoter increased conversion and selectivity and improved the hydrogen efficiency of the process.

Catalysts 5a–5d and 5g–h were regenerated by heating to 350° C. in a mixture of oxygen (10 percent) in helium. After regeneration, the catalysts were tested in the hydro-oxidation of propylene with the results shown in Table VI. Under similar process conditions, the regenerated catalysts showed an activity and selectivity which were comparable to or better than that of the fresh catalysts.

The activity of catalysts 5a and 5b after regeneration were monitored as a function of time with the results shown in Table VII.

TABLE VII

Activity of Regenerated Catalysts 5a and 5b[a]

| | 5(a) - 5 wt % Ag(Na)/TiO$_2$ | | | 5(b) - 5 wt % Ag(Cs)/TiO$_2$ | | |
|---|---|---|---|---|---|---|
| Hours on stream | Sel (mol %) | Conv (mol %) | H$_2$O/PO | Sel (mol %) | Conv (mol %) | H$_2$O/PO |
| 0.10 | 100.00 | 0.232 | 37.6 | 92.3 | 0.026 | 882 |
| 0.32 | 100.00 | 0.187 | 24.7 | 92.3 | 0.067 | 318 |
| 0.53 | 100.00 | 0.200 | 22.1 | 94.3 | 0.090 | 147 |
| 0.75 | 99.47 | 0.207 | 20.9 | 94.7 | 0.059 | 153 |
| 0.97 | 99.00 | 0.218 | 19.8 | 93.4 | 0.063 | 151 |
| 1.18 | 100.00 | 0.213 | 18.9 | | | |
| 1.40 | 100.00 | 0.219 | 19.1 | | | |
| 1.62 | 99.49 | 0.214 | 18.8 | 86.4 | 0.071 | 158 |
| 1.82 | 100.00 | 0.219 | 18.0 | | | |
| 2.03 | 98.97 | 0.212 | 18.3 | | | |
| 2.25 | 98.95 | 0.208 | 18.4 | 83.8 | 0.081 | 145 |
| 2.47 | 98.48 | 0.216 | 16.9 | | | |
| 2.68 | 99.49 | 0.214 | 17.8 | | | |
| 2.90 | 98.98 | 0.215 | 16.9 | | | |
| 3.12 | 99.00 | 0.218 | 16.7 | | | |
| 3.33 | 98.97 | 0.212 | 17.1 | 81.8 | 0.069 | 155 |
| 18.38 | 93.10 | 0.095 | 25.0 | | | |
| 18.60 | 94.57 | 0.100 | 23.9 | | | |

[a]Feedstream (mol %): 11% hydrogen, 10% oxygen, 30% propylene, balance helium; 80° C.; flow 150 cc/min; atmospheric pressure.

It is seen in Table VII that regenerated catalysts 5(a) and 5(b) maintained a high selectivity to propylene oxide and a good conversion of propylene over a run time of 18 hours.

Catalyst 5(a) comprising sodium-promoted silver on titania was regenerated a second time by heating at 350° C. in a mixture of oxygen (10 percent) in helium. The catalyst was tested after this regeneration in the hydro-oxidation process at various temperatures with the results shown in Table VIII.

TABLE VIII

Activity of Catalyst 5(a) after Two Regenerations[a]

| Temperature ° C. | Conv. (mol %) | Sel (mol %). | H$_2$O/PO | |
|---|---|---|---|---|
| 50 | 0.013 | 100.0 | 23 | first run |
| 60 | 0.098 | 100.0 | 20 | first run |
| 70 | 0.164 | 100.0 | 19 | first run |
| 80 | 0.217 | 100.0 | 20 | first run |
| 80 | 0.201 | 100.0 | 20 | *after regen |
| 90 | 0.249 | 99.1 | 21 | *after regen |
| 100 | 0.270 | 88.6 | 27 | *after regen |
| 110 | 0.312 | 82.1 | 38 | *after regen |

[a]Feedstream (mol %): 11% hydrogen, 10% oxygen, 30% propylene, balance helium; Catalyst 5a: 5% Ag(Na)/TiO$_2$; flow 150 cc/min; atmospheric pressure.

It is seen in Table VIII that the sodium-promoted silver catalyst, which was regenerated two times, maintained a good conversion and high selectivity after each regeneration. The catalyst was active and selective at 110° C. Elemental analysis, as analyzed by NAA for 5(a) after use was the following: 4.10 percent silver; 1.07 percent sodium; and 55.0 percent titanium, as weight percentages.

Preparation of Titanosilicalite TS-1 having Si/Ti=100

Tetraethylorthosilicate (Fisher TEOS, 832.5 g) was weighed into a 4 liter stainless steel beaker and sparged with nitrogen gas for 30 minutes. Titanium n-butoxide (DuPont, Ti(O-n-Bu)$_4$) was injected from a syringe into the silicate. The weight of the titanium n-butoxide which was added to the TEOS was 14.07 g, taken by difference. A clear yellow solution was formed. The solution was heated and stirred under nitrogen for about 3 hours. The temperature varied from 50° C. to 130° C. The solution was then chilled in an ice bath.

A 40 weight percent solution of tetrapropylammonium hydroxide (TPAOH, 710.75 g) was weighed into a polyethylene bottle, which was capped and placed in an ice bath. The TPAOH was added dropwise to the chilled TEOS solution with vigorous stirring by an overhead stirrer. After one-half of the TPAOH had been added, the TEOS solution was cloudy and began to thicken. Within five minutes the solution froze completely. At this point the remainder of the TPAOH was added, the gel was broken up with a spatula, and stirring was resumed. Deionized water (354 g) was added, and the solution was warned to room temperature. After 5 hours the solids had largely dissolved, and an additional quantity of deionized water (708 g) was added. Stirring was continued overnight yielding a clear yellow synthesis gel containing no solids.

The synthesis gel was poured into a 1 gallon (3.785 liters) stainless steel autoclave and sealed. The autoclave was heated to 120° C. and then gradually to 160° C. where it was kept for 6 days. The reactor contents were stirred at all times. At the end of the reaction period, the autoclave was cooled and a milky white suspension was recovered. The solids were recovered, washed, centrifuged, and re-suspended in deionized water. The solids were filtered, dried at room temperature, heated slowly to 550° C., and calcined thereat for 8 hours. The solid was identified as having an MFI structure, as determined by XRD. Raman spectra did not reveal any crystalline titania. A Si/Ti atomic ratio of 100 was found, as measured by X-ray fluorescence (XRF). Yield of titanium silicalite: 106 g.

Example 6

The titanosilicate TS-1 support, prepared as described hereinabove, was loaded with silver and sodium promoter in the manner described in Example 5(a). The reagents used were as follows: TS-1 support (5.25.g); silver nitrate (0.3833 g); sodium nitrate (0.1590 g). The sodium/silver atomic ratio was 0.83. The catalyst prepared was tested in the hydro-oxidation of propylene to propylene oxide with the results shown in Table IX.

TABLE IX

Activity of Silver
(Sodium Promoted) on Ti-Containing Supports[a]

| Example | Support | Promoter | Hours on Stream | Sel (mol %) | Conv (mol %) | $H_2O$/PO |
|---|---|---|---|---|---|---|
| 80° C. | | | | | | |
| 6 | TS1 | Na | 0.30 | 81.8 | 0.024 | 252.5 |
| 7 | Ti/SiO$_2$ | Na | 0.88 | 58.1 | 0.034 | 157.5 |
| 90° C. | | | | | | |
| 6 | TS1 | Na | 1.28 | 70.2 | 0.135 | 67.2 |
| 7 | Ti/SiO$_2$ | Na | 1.88 | 69.8 | 0.047 | 108.7 |
| Stay at 90° C. | | | | | | |
| 6 | TS1 | Na | 2.28 | 88.2 | 0.304 | 18.0 |
| 7 | Ti/SiO$_2$ | Na | 2.88 | 80.0 | 0.049 | 75.9 |
| Stay at 90° C. | | | | | | |
| 6 | TS1 | Na | 3.28 | 92.5 | 0.318 | 13.0 |
| 7 | Ti/SiO$_2$ | Na | 3.88 | 82.5 | 0.044 | 70.8 |
| Stay at 90° C. | | | | | | |
| 6 | TS1 | Na | 4.28 | 94.1 | 0.295 | 12.5 |
| 7 | Ti/SiO$_2$ | Na | 4.87 | 85.7 | 0.038 | 74.0 |
| Stay at 90° C. | | | | | | |
| 6 | TS1 | Na | 5.27 | 92.5 | 0.332 | 15.1 |

[a]Feedstream (mol %): 11% hydrogen, 10% oxygen, 30% propylene, balance helium; Catatyst 6: 5% Ag(Na)/TS-1; Catalyst 7: 5% Ag(Na)/Ti/SiO$_2$; flow 150 cc/min; atmospheric pressure.

It is seen that a catalyst comprising silver and sodium on titanosilicate TS-1 is active and selective in the hydro-oxidation of propylene to propylene oxide over the run time of more than 5 hours. The catalyst of Example 6 was regenerated by heating to 350° C. in a mixture of oxygen (14 percent) in helium and holding at 350° C. for 1 hour. The regenerated catalyst was tested in the hydro-oxidation of propylene to propylene oxide in the manner described in Example 1. The regenerated catalyst remained active throughout a total run time of 9 hours. At 9 hours, the conversion of propylene at 100° C. was 0.070 percent and the selectivity to propylene oxide was 93.8 percent. The water to molar ratio was 25.6.

Example 7

A catalyst was prepared comprising silver and sodium on a support of titanium dispersed on silica. The support was obtained from PQ Corporation and comprised silica beads (Xerogel silica beads 4 mm dia.) having titanium deposited thereon. The support was pretreated to 600° C. in nitrogen and held for 1 hour and then calcined at 600° C. in an oxygen (10%) mixture in helium for four hours. The support was then cooled, crushed, and loaded with silver and sodium, as described in Example 5(a). The amounts of reagents were as follows: Ti/silica support, 5.26 g; silver nitrate, 0.3877 g; sodium nitrate, 0.1604 g. The sodium/silver atomic ratio was 0.83.

The catalyst was tested in the hydro-oxidation of propylene to propylene oxide, as described in Example 1, with the results shown in Table IX. It is seen that a catalyst comprising silver and sodium on a support of titanium dispersed on silica was active and selective in the hydro-oxidation of propylene to propylene oxide. At 90° C., conversion of propylene was 0.038 percent at a selectivity to propylene oxide of 85.7 percent.

Example 8

A catalyst was prepared to test the effect of gold with silver and sodium on titania. Chloroauric acid [0.3767 g of HAuCl$_4$.xH$_2$O (49.28% Au)] was dissolved in water (800 ml) and heated to 70° C. The pH of the solution was adjusted to 7.5 sodium carbonate. Next titanium dioxide (15.04 g of Degussa P25 TiO$_2$) was added to the solution and the pH adjusted to 7.5 with sodium carbonate. The mixture was stirred for 1 hour at 70° C. then cooled to room temperature. The solids were filtered. The solids were resuspended in water (500 cc) and stirred for 5 minutes, then filtered. The solids were dried at 110° C. for 4 hours, then crushed to a powder. This gold on titania material was added to a water solution (60 cc) containing silver nitrate (1.1230 g) and sodium nitrate (0.4856 g). The mixture was stirred for 1 hour at room temperature. The flask containing the gold on titania and the silver and sodium solution was put into an oven at 110° C. overnight to dry the material. The dried material was crushed and then calcined from room temperature to 500° C. in 4 hours and held at 500° C. for 5 hours in oxygen (20 percent) in helium. The materials were cooled to 80° C. then heated in hydrogen (5 percent) in helium from 80° to 300° C. in 4 hours and held at 300° C. for 4 hours to yield a catalyst of the invention. Elemental analysis, as analyzed by NAA for the fresh catalyst of this example was the following: 4.04 percent silver; 0.85 percent gold; 1.10 percent sodium; and 54.3 percent titanium, as weight percentages.

The catalyst was tested in the hydro-oxidation of propylene to propylene oxide in the manner described in Example 1 with the results shown in Table X.

TABLE X

4% Ag and 0.9% Au and Na on TiO$_2$

| T (° C.) | Hours on Stream | Sel (mol %) | Conv (mol %) | $H_2O$/PO |
|---|---|---|---|---|
| 50 | 0.70 | 100.0 | 0.069 | 12 |
| 60 | 1.70 | 100.0 | 0.114 | 17 |
| 70 | 2.68 | 100.0 | 0.244 | 12 |
| 80 | 3.88 | 89.7 | 0.348 | 12 |
| 80 | 4.88 | 87.5 | 0.287 | 15 |
| 90 | 5.87 | 80.3 | 0.322 | 18 |
| 90 | 6.87 | 80.4 | 0.266 | 22 |
| Regenerate @ 350° C.: | | | | |
| 80 | 0.10 | 100.0 | 0.945 | 2.1 |
| 80 | 0.32 | 100.0 | 0.410 | 11 |
| 80 | 0.53 | 100.0 | 0.367 | 8.3 |
| 80 | 0.75 | 99.5 | 0.434 | 7.7 |
| 80 | 1.17 | 99.2 | 0.469 | 6.3 |
| 80 | 1.60 | 98.9 | 0.465 | 6.3 |
| 80 | 1.82 | 98.0 | 0.424 | 6.5 |
| 80 | 2.25 | 94.5 | 0.395 | 6.7 |
| 80 | 2.68 | 92.9 | 0.357 | 7.7 |
| 80 | 3.10 | 91.8 | 0.335 | 8.3 |
| 80 | 3.53 | 90.7 | 0.319 | 8.8 |
| 80 | 4.18 | 91.8 | 0.271 | 8.9 |

(a) Feedstream (mol %): 11% hydrogen, 10% oxygen, 30% propylene, balance helium; flow 150 cc/min; atmospheric pressure.

From Table X it is seen that a catalyst comprising silver, gold, and sodium on titania is active and selective in the hydro-oxidation of propylene to propylene oxide. Hydrogen efficiency is also good.

Example 9

Ten catalysts were prepared to test the effect of both the silver loading and the sodium loading on the titania (Degussa P25). In one set of catalysts, the silver loading was kept constant at about 5 weight percent. In the other set of catalysts, the sodium loading was kept constant at about 1.6 weight percent. The reagents and the quantities of each used in the preparation are shown in Table XI. The preparation method was similar to Example 4 with the exception that the calcination profile was as follows: Calcined from room temperature to 500° C. in 4 hours and held at 500° C. for 4 hours in 20 percent oxygen in helium. Then, the materials were cooled to room temperature, heated in 5 percent hydrogen in helium from room temperature to 300° C. in 4 hours and held at 300° C. for 4 hours.

TABLE XI

Reagents used for Ag and Na on P25 $TiO_2$

| Example | $TiO_2$ | $AgNO_3$ | $NaNO_3$ | Na/Ag |
|---|---|---|---|---|
| 9a | 15.02 g | 1.1293 g | 0.1216 g | 0.22 |
| 9b | 15.01 g | 1.1262 g | 0.2442 g | 0.43 |
| 9c | 15.00 g | 1.1275 g | 0.4851 g | 0.86 |
| 9d | 15.01 g | 1.1289 g | 0.9749 g | 1.7 |
| 9e | 15.00 g | 1.1262 g | 2.0620 g | 3.7 |
| 9f | 15.00 g | 0.2553 g | 1.0044 g | 7.9 |
| 9g | 15.01 g | 0.5020 g | 1.0046 g | 4.0 |
| 9h | 15.00 g | 1.0005 g | 1.0034 g | 2.0 |
| 9i | 15.01 g | 2.1082 g | 1.0025 g | 0.95 |
| 9j | 15.00 g | 4.6230 g | 1.0045 g | 0.43 |

Catalyst samples 9a–9j were tested in the hydro-oxidation of propylene to propylene oxide in the manner described in Example 1, with the results shown in Table XII.

TABLE XII

Ag(Na)/$TiO_2$ Reactivity at Various Temperatures[a]

| Example | Na/Ag | Time (h) | Sel (mol %) | Conv (mol %) | $H_2O$/PO |
|---|---|---|---|---|---|
| 50° C. | | | | | |
| 9a | 0.22 | 0.10 | 80.8 | 0.026 | 18.1 |
| 9b | 0.43 | 0.28 | 95.7 | 0.056 | 20.2 |
| 9c | 0.86 | 0.47 | 91.3 | 0.021 | 88.9 |
| 9d | 1.7 | 0.65 | | 0.000 | |
| 9e | 3.7 | 0.83 | | 0.000 | |
| 60° C. | | | | | |
| 9a | 0.22 | 1.02 | 91.4 | 0.127 | 30.2 |
| 9b | 0.43 | 1.20 | 97.7 | 0.163 | 25.9 |
| 9c | 0.86 | 1.38 | 97.2 | 0.071 | 40.7 |
| 9d | 1.7 | 1.57 | 100.0 | 0.020 | 36.7 |
| 9e | 3.7 | 1.75 | | 0.000 | |
| 70° C. | | | | | |
| 9a | 0.22 | 1.93 | 86.5 | 0.103 | 48.4 |
| 9b | 0.43 | 2.12 | 90.0 | 0.149 | 36.6 |
| 9c | 0.86 | 2.30 | 98.3 | 0.107 | 32.3 |
| 9d | 1.7 | 2.47 | 100.0 | 0.075 | 21.9 |
| 9e | 3.7 | 2.65 | | 0.000 | |
| 80° C. | | | | | |
| 9a | 0.22 | 2.83 | 87.3 | 0.078 | 60.3 |
| 9b | 0.43 | 3.02 | 81.2 | 0.136 | 57.3 |
| 9c | 0.86 | 3.20 | 98.9 | 0.184 | 25.8 |
| 9d | 1.7 | 3.38 | 100.0 | 0.111 | 18.0 |
| 9e | 3.7 | 3.57 | | 0.000 | |
| 9f | 7.9 | 0.10 | | 0.000 | |
| 9g | 4 | 0.30 | 100.0 | 0.026 | 27.0 |
| 9h | 2 | 0.50 | 94.3 | 0.038 | 40.7 |
| 9i | 0.95 | 0.70 | 100.0 | 0.077 | 18.7 |
| 9j | 0.43 | 0.90 | 100.0 | 0.047 | 27.1 |
| 90° C. | | | | | |
| 9a | 0.22 | 3.75 | 80.8 | 0.024 | 142.3 |
| 9b | 0.43 | 3.93 | 77.4 | 0.095 | 79.4 |
| 9c | 0.86 | 4.12 | 98.4 | 0.174 | 28.0 |
| 9d | 1.7 | 4.30 | 100.0 | 0.167 | 16.3 |
| 9e | 3.7 | 4.48 | 100.0 | 0.006 | 47.0 |
| 9f | 7.9 | 1.10 | 100.0 | 0.119 | 10.1 |
| 9g | 4 | 1.30 | 100.0 | 0.136 | 15.0 |
| 9h | 2 | 1.50 | 95.7 | 0.074 | 31.0 |
| 9i | 0.95 | 1.70 | 100.0 | 0.132 | 15.9 |
| 9j | 0.43 | 1.90 | 100.0 | 0.048 | 36.1 |
| 100° C. | | | | | |
| 9a | 0.22 | 4.67 | 63.2 | 0.019 | 230.3 |
| 9b | 0.43 | 4.85 | 73.6 | 0.055 | 117.8 |
| 9c | 0.86 | 5.03 | 90.9 | 0.164 | 32.4 |
| 9d | 1.7 | 5.22 | 99.0 | 0.206 | 17.2 |
| 9e | 3.7 | 5.38 | 100.0 | 0.006 | 42.5 |
| 9f | 7.9 | 2.10 | 100.0 | 0.147 | 14.3 |
| 9g | 4 | 2.30 | 100.0 | 0.184 | 16.4 |
| 9h | 2 | 2.48 | 98.2 | 0.122 | 24.9 |
| 9i | 0.95 | 2.68 | 99.4 | 0.171 | 17.0 |
| 9j | 0.43 | 2.88 | 100.0 | 0.104 | 24.7 |
| 110° C. | | | | | |
| 9c | 0.86 | 5.58 | 75.0 | 0.183 | 46.3 |
| 9d | 1.7 | 5.78 | 98.5 | 0.210 | 21.2 |
| 9e | 3.7 | 5.98 | 100.0 | 0.018 | 79.7 |
| 9f | 7.9 | 3.08 | 100.0 | 0.159 | 15.7 |
| 9g | 4 | 3.28 | 98.3 | 0.193 | 19.1 |
| 9h | 2 | 3.48 | 98.0 | 0.159 | 23.5 |
| 9i | 0.95 | 3.68 | 95.1 | 0.183 | 20.3 |
| 9j | 0.43 | 3.88 | 93.9 | 0.128 | 26.5 |
| 120° C. | | | | | |
| 9d | 1.7 | 6.18 | 81.1 | 0.163 | 48.1 |
| 9e | 3.7 | 6.38 | 100.0 | 0.024 | 79.0 |
| 9f | 7.9 | 4.08 | 85.4 | 0.140 | 23.0 |
| 9g | 4 | 4.28 | 76.2 | 0.212 | 27.6 |
| 9h | 2 | 4.48 | 87.0 | 0.165 | 39.6 |
| 9i | 0.95 | 4.68 | 77.1 | 0.158 | 28.8 |
| 9j | 0.43 | 4.88 | 72.7 | 0.129 | 33.3 |
| 130° C. | | | | | |
| 9e | 3.7 | 6.72 | 100.0 | 0.023 | 78.1 |
| 140° C. | | | | | |
| 9e | 3.7 | 7.05 | 100.0 | 0.044 | 64.7 |
| 150° C. | | | | | |
| 9e | 3.7 | 7.38 | 100.0 | 0.045 | 66.6 |
| 160° C. | | | | | |
| 9e | 3.7 | 7.72 | 71.4 | 0.058 | 96.5 |

Regenerated at 400° C. with 10% $O_2$, 1.5% $H_2O$; Cooled back to 100° C., then stopped added $H_2O$

| | | | | | |
|---|---|---|---|---|---|
| 100° C. | | | | | |
| 9f | 7.9 | 0.10 | 100.0 | 0.096 | 14.9 |
| 9g | 4 | 0.30 | 100.0 | 0.064 | 97.0 |
| 9h | 2 | 0.50 | 54.0 | 0.121 | 80.3 |
| 9i | 0.95 | 0.70 | 100.0 | 0.209 | 20.1 |
| 9j | 0.43 | 0.90 | 100.0 | 0.157 | 22.8 |
| 100° C. | | | | | |
| 9f | 7.9 | 1.10 | 100.0 | 0.206 | 10.1 |
| 9g | 4 | 1.30 | 100.0 | 0.209 | 18.5 |
| 9h | 2 | 1.50 | 99.0 | 0.189 | 16.1 |
| 9i | 0.95 | 1.70 | 100.0 | 0.220 | 15.0 |
| 9j | 0.43 | 1.90 | 100.0 | 0.186 | 21.1 |

TABLE XII-continued

Ag(Na)/TiO$_2$ Reactivity at Various Temperatures[a]

| Example | Na/Ag | Time (h) | Sel (mol %) | Conv (mol %) | H$_2$O/PO |
|---|---|---|---|---|---|
| 100° C. | | | | | |
| 9f | 7.9 | 2.10 | 100.0 | 0.173 | 10.9 |
| 9g | 4 | 2.30 | 100.0 | 0.221 | 17.1 |
| 9h | 2 | 2.50 | 89.5 | 0.165 | 21.1 |
| 9i | 0.95 | 2.70 | 98.8 | 0.167 | 17.6 |
| 9i | 0.43 | 2.88 | 98.5 | 0.137 | 20.6 |

[a]Feedstream (mol %): 11% hydrogen, 10% oxygen, 30% propylene, balance helium; Catalyst: Ag(Na)/TiO$_2$; flow 150 cc/min; atmospheric pressure.

It is seen that compositions comprising silver, a promoter selected from Group 1, Group 2, or the lanthanides, and titanium dioxide functioned as catalysts in the hydro-oxidation of propylene to propylene oxide. When Example 9 is compared with Examples 1 and 2, it is seen that the addition of the promoter increased conversion and selectivity and improved the hydrogen efficiency of the process. When a higher amount of sodium was used, a lower amount [about 1 weight percent] of silver provided an active catalyst, as in 9f.

Catalysts 9f–9j were regenerated by heating to 400° C. in a mixture of oxygen (10 percent) and water (1.5 percent) in helium. Under similar process conditions, the regenerated catalysts showed an activity and selectivity which were comparable to or better than that of the fresh catalysts, as shown in Table XII.

Example 10

The catalyst of 9 g was also used in the hydro-oxidation of trans-2-butene to 2,3-butylene oxide. The catalyst (5 g) was loaded into a 10 cc fixed-bed, continuous flow reactor with flows of helium, oxygen, hydrogen, and trans-2-butene. Total flow rate was 100 cc/min (or GHSV 1,200 h$^{-1}$). Feedstream composition was 6.4 percent hydrogen, 7.6 percent oxygen, 30 percent trans-2-butene, and the balance helium. Trans-2-butene and helium were used as pure streams; hydrogen was mixed with helium in a 20 H$_2$/80 He (v/v) mixture; oxygen was mixed with helium in a 20 O$_2$/80 He (v/v) mixture. Pressure was atmospheric; temperatures are shown in Table XIII. Products were analyzed using an on-line gas chromatograph (Chrompack™ Poraplot™ S column, 25 m) with the results shown in Table XIII. The catalyst was regenerated by heating at 350° C. in a flow of oxygen (13 percent) in helium of 75 cc/min (GHSV 900 h$^{-1}$) for about 12 hours. The regenerated catalyst was retested in the oxidation of trans-2-butene with the results shown in Table XIII.

TABLE XIII

Direct Oxidation of trans-2-butene (BB) to
2,3 Butene Oxide (BO) Over Ag (Na)/TiO$_2$ Catalyst[a]

| T (° C.) | Hours on Stream | Sel BO (mol %) | Conv BB (mol %) |
|---|---|---|---|
| 80 | 0.7 | 100.0 | 0.186 |
| 80 | 3.2 | 100.0 | 0.223 |
| 100 | 4.2 | 100.0 | 0.513 |
| 120 | 5.0 | 100.0 | 1.016 |
| 140 | 6.2 | 97.9 | 1.358 |

TABLE XIII-continued

Direct Oxidation of trans-2-butene (BB) to
2,3 Butene Oxide (BO) Over Ag (Na)/TiO$_2$ Catalyst[a]

| T (° C.) | Hours on Stream | Sel BO (mol %) | Conv BB (mol %) |
|---|---|---|---|
| Regenerate @ 350° C.: | | | |
| 100 | 0.5 | 100.0 | 0.407 |
| 100 | 3.0 | 100.0 | 0.487 |
| 100 | 4.0 | 100.0 | 0.510 |
| 100 | 5.0 | 100.0 | 0.503 |
| 140 | 5.9 | 96.7 | 1.224 |
| 160 | 6.8 | 85.2 | 0.943 |

[a]Feedstream (mol %): 6.4% hydrogen, 7.6% oxygen, 30% trans-2-butene, balance helium; flow 100 cc/min; atmospheric pressure.

From Table XIII it is seen that a catalyst comprising silver and sodium on titania is active and selective in the hydro-oxidation of trans-2-butene to 2,3-butene oxide.

Example 11

Five catalyst were prepared to test the effect of mixed promoters (P) with a catalyst comprising silver on titania (Degussa P25). The reagents and the quantities of each used in the preparation are shown in Table XIV. The silver and the sodium were kept constant on the titania. The amount of the second promoter nitrate was kept constant in each sample. The preparation method was similar to Example 4 with the exception that the calcination profile was as follows: Calcined from room temperature to 500° C. in 4 hours and held at 500° C. for 4 hours in 20 percent oxygen in helium. Then, the materials were cooled to 75° C., heated in 5 percent hydrogen in helium from 75° to 300° C. in 4 hours and held at 300° C. for 4 hours.

TABLE XIV

Reagents used for Ag and (Mixed Promoter) on P25 TiO$_2$

| Example | TiO$_2$ | AgNO$_3$ | NaNO$_3$ | 2$^{nd}$ Promoter Nitrate |
|---|---|---|---|---|
| 11a | 15.02 g | 1.1199 g | 0.4822 g | Ca(NO$_3$)$_2$.4H$_2$O 0.4937 g |
| 11b | 15.02 g | 1.1200 g | 0.4803 g | Ba(NO$_3$)$_2$ 0.5003 g |
| 11c | 15.01 g | 1.1240 g | 0.4820 g | La(NO$_3$)$_3$.6H$_2$O 0.4927 g |
| 11d | 15.01 g | 1.1211 g | 0.4804 g | Er(NO$_3$)$_3$.5H$_2$O 0.4987 g |
| 11e | 15.02 g | 1.1276 g | 0.4805 g | Lu(NO$_3$)$_3$.xH$_2$O 0.5040 g |

Catalyst samples 11a–11e were tested in the hydro-oxidation of propylene to propylene oxide, in the manner described in Example 1, with the results shown in Table XV.

TABLE XV

Ag(Mixed Promoter)/TiO$_2$ Reactivity at Various Temperatures[a]

| Example | Promoter | Hours | Sel (mol %) | Conv (mol %) | H$_2$O/PO |
|---|---|---|---|---|---|
| 50° C. | | | | | |
| 11b | Na + Ba | 0.30 | 100.0 | 0.013 | 47.5 |
| 11c | Na + La | 0.50 | 96.0 | 0.074 | 13.9 |
| 11d | Na + Er | 0.68 | 100.0 | 0.092 | 12.1 |

TABLE XV-continued

Ag(Mixed Promoter)/TiO$_2$ Reactivity at Various Temperatures[a]

| Example | Promoter | Hours | Sel (mol %) | Conv (mol %) | H$_2$O/PO |
|---|---|---|---|---|---|
| 11e 60° C. | Na + Lu | 0.88 | 100.0 | 0.097 | 12.5 |
| 11a | Na + Ca | 1.28 | 100.0 | 0.094 | 19.2 |
| 11b | Na + Ba | 1.48 | 100.0 | 0.114 | 18.7 |
| 11c | Na + La | 1.68 | 98.7 | 0.158 | 19.3 |
| 11d | Na + Er | 1.88 | 100.0 | 0.131 | 20.5 |
| 11e 70° C. | Na + Lu | 2.08 | 100.0 | 0.124 | 21.6 |
| 11a | Na + Ca | 2.28 | 100.0 | 0.147 | 21.0 |
| 11b | Na + Ba | 2.48 | 98.3 | 0.185 | 19.8 |
| 11c | Na + La | 2.68 | 98.9 | 0.179 | 25.4 |
| 11d | Na + Er | 2.88 | 100.0 | 0.204 | 19.4 |
| 11e 80° C. | Na + Lu | 3.07 | 100.0 | 0.186 | 22.3 |
| 11a | Na + Ca | 3.28 | 98.9 | 0.184 | 23.1 |
| 11b | Na + Ba | 3.47 | 98.4 | 0.264 | 18.8 |
| 11c | Na + La | 3.67 | 98.7 | 0.246 | 25.5 |
| 11d | Na + Er | 3.87 | 98.7 | 0.244 | 23.5 |
| 11e 90° C. | Na + Lu | 4.07 | 96.4 | 0.233 | 24.5 |
| 11a | Na + Ca | 4.27 | 94.0 | 0.253 | 27.4 |
| 11b | Na + Ba | 4.47 | 90.9 | 0.320 | 23.5 |
| 11c | Na + La | 4.67 | 82.3 | 0.221 | 43.3 |
| 11d | Na + Er | 4.87 | 88.2 | 0.236 | 31.7 |
| 11e 100° C. | Na + Lu | 5.07 | 85.1 | 0.215 | 36.2 |
| 11a | Na + Ca | 5.27 | 76.1 | 0.212 | 45.8 |
| 11b | Na + Ba | 5.47 | 84.4 | 0.299 | 29.3 |
| 11c | Na + La | 5.67 | 75.4 | 0.196 | |
| 11d | Na + Er | 5.87 | 77.8 | 0.222 | 46.5 |
| 11e Regenerate at 350° C. 90° C. | Na + Lu | 6.07 | 77.9 | 0.158 | 51.9 |
| 11b | Na + Ba | 0.10 | 99.3 | 0.547 | 8.1 |
| 11b | Na + Ba | 0.32 | 99.4 | 0.328 | 17.1 |
| 11b | Na + Ba | 0.52 | 99.1 | 0.347 | 16.4 |
| 11b | Na + Ba | 0.73 | 98.9 | 0.361 | 15.3 |
| 11b | Na + Ba | 0.95 | 98.9 | 0.362 | 15.4 |
| 11b | Na + Ba | 1.17 | 98.6 | 0.358 | 15.1 |
| 11b | Na + Ba | 1.38 | 97.9 | 0.351 | 15.3 |
| 11b | Na + Ba | 1.60 | 97.3 | 0.341 | 14.6 |
| 11b | Na + Ba | 1.82 | 96.2 | 0.320 | 16.1 |

[a]Feedstream (mol %): 11% hydrogen, 10% oxygen, 30% propylene, balance helium; flow 150 cc/min; atmospheric pressure.

It is seen that compositions comprising silver, a mixture of promoters selected from Group 1, Group 2, or the lanthanides, and titanium dioxide functioned as catalysts in the hydro-oxidation of propylene to propylene oxide. When Examples 11a–11e are compared with Examples 1 and 2 and Examples 5c, d, e, g, h, it is seen that the addition of a second promoter increased conversion and/or selectivity and/or improved the hydrogen efficiency of the process.

Catalysts 11a–11a were regenerated by heating to 350° C. in a mixture of oxygen (10 percent) in helium. Under similar process conditions, the regenerated catalysts showed an activity and selectivity which were comparable to or better than that of the fresh catalysts.

The activity of the catalyst 11b after regeneration was monitored as a function of time with the results shown in Table XV.

Example 12

The following amounts of reagents were used: titanium dioxide (Degussa Formed P25 anatase, Support 7701 4.5× 4.5 mm tablets 92.5 g), silver nitrate (7.0800 g), sodium nitrate (3.0256 g) and water (27 cc). The pellets were impregnated with the solution and then rotated in the excess solution. The material was dried at 110° C. with mixing until it appeared dry, then dried at 100° C. over night. The resulting dried material was then calcined from room temperature to 500° C. in 2 hours and held at 500° C. for 4 hours in a mixture of oxygen (20 percent) in helium. The calcined material was cooled to room temperature, then heated in a mixture of hydrogen (5 percent) in helium from room temperature to 300° C. in 4 hours and held at 300° C. for 4 hours. The catalyst was crushed and the 20–40 mesh portion was tested in the hydro-oxidation of propylene to propylene oxide with the results shown in Table XVI.

TABLE XVI

Direct Oxidation of Propylene (PP) to Propylene Oxide (PO) Over Ag (Na)/TiO$_2$ Catalyst[a]

| Ex. | Time on Stream | Conv PP (mol %) | Sel PO (mol %) | H$_2$O/PO |
|---|---|---|---|---|
| 12 | 30 min | 0.246 | 90.8 | 29 |
| 12 | 40 min | 0.233 | 71.6 | 43 |
| 12 | 50 min | 0.225 | 70.1 | 43 |
| 12 | 60 min | 0.232 | 68.7 | 45 |
| 12 | 70 min | 0.230 | 68.8 | 47 |
| 12 | 80 min | 0.229 | 69.8 | 45 |
| 12 | 90 min | 0.216 | 70.1 | 44 |

[a]Feedstream (mol %): 7% H$_2$, 7% O$_2$, 30% propylene, balance helium; flow 2000 cc/min; 125° C.; pressure: 250 psia; 5 wt percent Ag (Na) on TiO$_2$ 20–40 mesh.

It is seen that a composition comprising silver and sodium on titanium dioxide is capable of catalyzing the hydro-oxidation of propylene to propylene oxide at 250 psia.

What is claimed is:

1. A process of preparing an olefin oxide comprising contacting an olefin having at least three carbon atoms with oxygen in the presence of hydrogen and an optional diluent, and in the presence of a catalyst comprising silver and titanium.

2. The process of claim 1 wherein the olefin is a $C_{3-12}$ olefin.

3. The process of claim 2 wherein the olefin is propylene.

4. The process of claim 1 wherein the olefin is selected from the group consisting of butadiene, cyclopentadiene, dicyclopentadiene, styrene, (α-methylstyrene, divinylbenzene, allyl chloride, allyl alcohol, diallyl ether, allyl ethyl ether, allyl butyrate, allyl acetate, allyl benzene, allyl phenyl ether, allyl propyl ether, and allyl anisole.

5. The process of claim 1 wherein the olefin is used in a quantity greater than 1 and less than 99 mole percent, based on the total moles of olefin, oxygen, hydrogen, and optional diluent.

6. The process of claim 1 wherein the oxygen is used in a quantity greater than 0.01 and less than 30 mole percent, based on the total moles of olefin, oxygen, hydrogen, and optional diluent.

7. The process of claim 1 wherein the hydrogen is used in a quantity greater than 0.01 and less than 50 mole percent, based on the total moles of olefin, oxygen, hydrogen, and optional diluent.

8. The process of claim 1 wherein a diluent is employed.

9. The process of claim 8 wherein when the process is conducted in a vapor phase, the diluent is selected from helium, nitrogen, argon, methane, carbon dioxide, steam and mixtures thereof; and wherein when the process is conducted in a liquid phase, the diluent is selected from aromatics, aliphatic alcohols, chlorinated aliphatic alkanols, and liquid polyethers, polyalcohols, and polyesters.

10. The process of claim 8 wherein the diluent is used in a quantity greater than 0 and less than 90 mole percent, based on the total moles of olefin, oxygen, hydrogen, and diluent.

11. The process of claim 1 wherein the silver is loaded onto the catalyst in an amount greater than 0.01 and less than 20 weight percent, based on the total weight of the catalyst.

12. The process of claim 1 wherein the catalyst further comprises a promoter element.

13. The process of claim 12 wherein the promoter element is selected from the group consisting of Group 1, Group 2, zinc, cadmium, the lanthanide rare earths, the actinides, and combinations thereof.

14. The process of claim 12 wherein the promoter element is selected from the group consisting of lithium, sodium, potassium, rubidium, cesium, magnesium, calcium, barium, erbium, lutetium, and combinations thereof.

15. The process of claim 12 wherein the catalyst comprises at least one Group 1 element in combination with a Group 2 element and/or a lanthanide element.

16. The process of claim 12 wherein the promoter loading is greater than 0.01 and less than 40 weight percent, based on the total weight of the catalyst.

17. The process of claim 1 wherein the catalyst further comprises gold.

18. The process of claim 17 wherein the gold loading is greater than 0 and less than 20 weight percent, based on the total weight of the catalyst.

19. The process of claim 1 wherein the titanium is in the form of titanium dioxide or titanium dioxide supported on silica, alumina, or an aluminosilicate.

20. The process of claim 19 wherein the titanium dioxide is anatase or rutile.

21. The process of claim 1 wherein the titanium is in the form of a titanosilicate.

22. The process of claim 21 wherein the titanosilicate is porous.

23. The process of claim 22 wherein the porous titanosilicate is a microporous or mesoporous titanosilicate having pores in the range from 4 Å to 500 Å.

24. The process of claim 23 wherein the titanosilicate is TS-1, TS-2, Ti-beta, Ti-ZSM-12, Ti-ZSM-48, or Ti-MCM-41.

25. The process of claim 1 wherein the titanium is in the form of a mixture of titanium dioxide and a porous titanosilicate.

26. The process of claim 1 wherein the titanium is in the form of a promoter metal titanate.

27. The process of claim 26 wherein the promoter metal titanate is magnesium titanate, calcium titanate, barium titanate, strontium titanate, sodium titanate, potassium titanate, erbium titanate, lutetium titanate, thorium titanate, or uranium titanate.

28. The process of claim 1 wherein the titanium is in the form of titanium dispersed on a support.

29. The process of claim 1 wherein the titanium is dispersed on silica, alumina, or an aluimnosilicate.

30. The process of claim 1 wherein the titanium is in the form of titanium dispersed on a promoter metal silicate.

31. The process of claim 1 wherein the titanium is in the form of a mixture whose components are selected from the group consisting of titanium dioxide, supported titanium dioxide, titanosilicates, promoter metal titanates, titanium dispersed on silica, alumina, and aluminosilicates, and titanium dispersed on promoter metal silicates.

32. The process of claim 1 wherein the process is conducted at a temperature greater than 20° C. and less than 250° C.

33. The process of claim 1 wherein the process is conducted at a pressure between atmospheric and 400 psig (2758 kPa).

34. The process of claim 1 wherein the process is conducted in a gaseous phase at a gas hourly space velocity of the olefin of greater than 1,000 h$^{-1}$ and less than 20,000 h$^{-1}$.

35. The process of claim 1 wherein the process is conducted in a liquid phase at a weight hourly space velocity of the olefin of greater than 0.1 h$^{-1}$ and less than 20 h$^{-1}$.

36. The process of claim 1 wherein the reactor is selected from fixed bed, transport bed, moving bed, fluidized bed, continuous flow, intermittent flow, trickle bed, shell and tube, and swing reactors.

37. The process of claim 1 wherein the olefin conversion is greater than 0.02 mole percent and the selectivity to olefin oxide is greater than 75 mole percent.

38. The process of claim 1 wherein the catalyst composition excludes the Group 8 metals of the Periodic Table.

39. The process of claim 1 wherein propylene is contacted with oxygen in a gas phase in the presence of hydrogen and an optional diluent and in the presence of a catalyst comprising titanium, silver, optionally gold, and optionally at least one promoter element selected from the group consisting of Group 1, Group 2, zinc, cadmium, the lanthanide rare earths, the actinide elements, and combinations thereof, the contacting being conducted at a temperature greater than 20° C. and less than 250° C. so as to prepare propylene oxide.

40. The process of claim 39 wherein the quantity of propylene is greater than 10 and less than 70 mole percent, based on the total moles of olefin, oxygen, hydrogen, and optional diluent.

41. The process of claim 39 wherein the quantity of oxygen is greater than 0.01 and less than 20 mole percent, based on the total moles of propylene, oxygen, hydrogen, and optional diluent.

42. The process of claim 39 wherein the quantity of hydrogen is greater than 0.01 and less than 50 mole percent, based on the total moles of propylene, oxygen, hydrogen, and optional diluent.

43. The process of claim 39 wherein the quantity of diluent is greater than 15 and less than 70 mole percent, based on the total moles of propylene, oxygen, hydrogen, and optional diluent.

44. The process of claim 39 wherein the propylene conversion is greater than 0.10 mole percent, and the selectivity to propylene oxide is greater than 90 mole percent.

45. The process of claim 17 wherein the catalyst further comprises a promoter element selected from the group consisting of Group 1 elements, Group 2 elements, zinc, cadmium, the lanthanide rare earths, the actinides, and combinations thereof.

* * * * *